(12) United States Patent　(10) Patent No.: US 9,730,660 B2
Suzuki　(45) Date of Patent: Aug. 15, 2017

(54) CONVERTING LOW-DOSE TO HIGHER DOSE MAMMOGRAPHIC IMAGES THROUGH MACHINE-LEARNING PROCESSES

(71) Applicant: Kenji Suzuki, Homewood, IL (US)

(72) Inventor: Kenji Suzuki, Homewood, IL (US)

(73) Assignee: ALARA SYSTEMS, INC., Mountain View, CA (US)

( * ) Notice: Subject to any disclaimer, the term of this patent is extended or adjusted under 35 U.S.C. 154(b) by 154 days.

(21) Appl. No.: 14/596,869

(22) Filed: Jan. 14, 2015

(65) Prior Publication Data

US 2015/0196265 A1　Jul. 16, 2015

Related U.S. Application Data

(60) Provisional application No. 61/927,745, filed on Jan. 15, 2014.

(51) Int. Cl.
*A61B 6/00*　　(2006.01)
*G06T 5/00*　　(2006.01)
(Continued)

(52) U.S. Cl.
CPC ............ *A61B 6/502* (2013.01); *A61B 6/5211* (2013.01); *G06K 9/6262* (2013.01); *G06T 5/001* (2013.01);
(Continued)

(58) Field of Classification Search
CPC combination set(s) only.
See application file for complete search history.

(56) References Cited

U.S. PATENT DOCUMENTS

| | | |
|---|---|---|
| 5,751,787 A | 5/1998 | Jing et al. |
| 6,158,888 A | 12/2000 | Walker et al. |

(Continued)

OTHER PUBLICATIONS

S. A. Feig and R. E. Hendrick, "Radiation risk from screening mammography of women aged 40-49 years," *J Natl Cancer Inst Monogr*, pp. 119-124, 1997.

(Continued)

*Primary Examiner* — Wyatt Stoffa
*Assistant Examiner* — Hsien Tsai
(74) *Attorney, Agent, or Firm* — Cooper & Dunham, LLP

(57) ABSTRACT

A method and system for converting low-dose mammographic images with much noise into higher quality, less noise, higher-dose-like mammographic images, using of a trainable nonlinear regression (TNR) model with a patch-input-pixel-output scheme, which can be called a call pixel-based TNR (PTNR). An image patch is extracted from an input mammogram acquired at a reduced x-ray radiation dose (lower-dose), and pixel values in the patch are entered into the PTNR as input. The output of the PTNR is a single pixel that corresponds to a center pixel of the input image patch. The PTNR is trained with matched pairs of mammograms, inputting low-dose mammograms together with corresponding desired standard x-ray radiation dose mammograms (higher-dose), which are ideal images for the output images. Through the training, the PTNR learns to convert low-dose mammograms to high-dose-like mammograms. Once trained, the trained PTNR does not require the higher-dose mammograms anymore. When a new reduced x-ray radiation dose (low dose) mammogram is entered, the trained PTNR would output a pixel value similar to its desired pixel value, in other words, it would output high-dose-like mammograms or "virtual high-dose" mammograms where noise and artifacts due to low radiation dose are substantially reduced, i.e., a higher image quality. With the (Continued)

"virtual high-dose" mammograms, the detectability of lesions and clinically important findings such as masses and microcalcifications can be improved.

37 Claims, 18 Drawing Sheets

(51) Int. Cl.
G06T 5/50 (2006.01)
G06K 9/62 (2006.01)
(52) U.S. Cl.
CPC ............... *G06T 5/50* (2013.01); *A61B 6/542* (2013.01); *G06T 2207/10116* (2013.01); *G06T 2207/20081* (2013.01); *G06T 2207/30068* (2013.01)

(56) References Cited

U.S. PATENT DOCUMENTS

| | | | | |
|---|---|---|---|---|
| 6,754,380 B1* | 6/2004 | Suzuki | ...................... | G06K 9/32 382/156 |
| 6,819,790 B2 | 11/2004 | Suzuki et al. | | |
| 7,412,024 B1 | 8/2008 | Yun et al. | | |
| 7,545,965 B2 | 6/2009 | Suzuki et al. | | |
| 8,378,302 B2 | 2/2013 | Pan et al. | | |
| 8,395,120 B2 | 3/2013 | Pan et al. | | |
| 2005/0100208 A1* | 5/2005 | Suzuki | ...................... | G06T 5/007 382/157 |
| 2008/0232667 A1* | 9/2008 | Kitamura | ................. | G06K 9/54 382/132 |
| 2014/0153819 A1* | 6/2014 | Lin | ......................... | G06T 5/002 382/159 |

OTHER PUBLICATIONS

U. S. P. S. T. Force, "Screening for breast cancer: recommendations and rationale," *Am Fam Physician*, vol. 65, pp. 2537-2544, Jun. 15, 2002.
M. J. Yaffe and J. G. Mainprize, "Risk of radiation-induced breast cancer from mammographic screening," *Radiology*, vol. 258, pp. 98-105, Jan. 2011.
S. Obenauer, K. P. Hermann, and E. Grabbe, "Dose reduction in full-field digital mammography: an anthropomorphic breast phantom study," *Br J Radiol*, vol. 76, pp. 478-482, Jul. 2003.
R. L. Smathers, J. M. Boone, L. J. Lee, E. A. Berns, R. A. Miller, and A. M. Wright, "Radiation dose reduction for augmentation mammography," *AJR Am J Roentgenol*, vol. 188, pp. 1414-1421, May 2007.
X. Liu, C. J. Lai, G. J. Whitman, W. R. Geiser, Y. Shen, Y. Yi, et al., "Effects of exposure equalization on image signal-to-noise ratios in digital mammography: a simulation study with an anthropomorphic breast phantom," *Med Phys*, vol. 38, pp. 6489-6501, Dec. 2011.
M. Yakabe, S. Sakai, H. Yabuuchi, Y. Matsuo, T. Kamitani, T. Setoguchi, et al., "Effect of dose reduction on the ability of digital mammography to detect simulated microcalcifications," *J Digit Imaging*, vol. 23, pp. 520-526, Oct. 2010.
W. Huda, K. M. Ogden, E. M. Scalzetti, D. R. Dance, and E. A. Bertrand, "How do lesion size and random noice affect detection performance in digital mammography?," *Acad Radiol*, vol. 13, pp. 1355-1366, Nov. 2006.
A. S. Chawla, E. Samei, R. Saunders, C. Abbey, and D. Delong, "Effect of dose reduction on the detection of mammographic lesions: a mathematical observer model analysis," *Med Phys*, vol. 34, pp. 3385-3398, Aug. 2007.
G. Gennaro, L. Katz, H. Souchay, C. Alberelli, and C. di Maggio, "Are phantoms useful for predicting the potential of dose reduction in full-field digital mammography?," *Phys Med Biol*, vol. 50, pp. 1851-1870, Apr. 21, 2005.

N. T. Ranger, J. Y. Lo, and E. Samei, "A technique optimization protocol and the potential for dose reduction in digital mammography," *Med Phys*, vol. 37, pp. 962-969, Mar. 2010.
E. Samei, R. S. Saunders, Jr., J. A. Baker, and D. M. Delong, "Digital mammography: effects of reduced radiation dose on diagnostic performance," , *Radiology*, vol. 243, pp. 396-404, May 2007.
K. C. Young, M. L. Ramsdale, and A. Rust, "Dose and image quality in mammography with an automatic beam quality system," *Br J Radiol*, vol. 69, pp. 555-562, Jun. 1996.
S. V. Destounis, P. DiNitto, W. Logan-Young, E. Bonaccio, M. L. Zuley, and K. M. Willison, "Can computer-aided detection with double reading of screening mammograms help decrease the false-negative rate? Initial experience," *Radiologogy*, vol. 232, pp. 578-584, Aug. 2004.
K. Suzuki, S. G. Armato, 3rd, F. Li, S. Sone, and K. Doi, "Massive training artificial neural network (MTANN) for reduction of false positives in computerized detection of lung nodules in low-dose computed tomography," *Med Phys*, vol. 30, pp. 1602-1617, Jul. 2003.
K. Suzuki, I. Horiba, and N. Sugie, "Efficient approximation of neural filters for removing quantum noise from images," *IEEE Transactions on Signal Processing*, vol. 50, pp. 1787-1799, Jul. 2002.
K. Suzuki, I. Horiba, and N. Sugie, "Neural edge enhancer for supervised edge enhancement from noisy images," *IEEE Transactions on Pattern Analysis and Machine Intelligence*, vol. 25, pp. 1582-1596, Dec. 2003.
H. Arimura, S. Katsuragawa, K. Suzuki, F. Li, J. Shiraishi, S. Sone, et al., "Computerized scheme for automated detection of lung nodules in low-dose computed tomography images for lung cancer screening," *Academic Radiology*, vol. 11, pp. 617-629, Jun. 2004.
F. Li, H. Arimura, K. Suzuki, J. Shiraishi, Q. Li, H. Abe, et al., "Computer-aided detection of peripheral lung cancers missed at CT: ROC analyses without and with localization," *Radiology*, vol. 237, pp. 684-690, Nov. 2005.
K. Suzuki, J. Shiraishi, H. Abe, H. MacMahon, and K. Doi, "False-positive reduction in computer-aided diagnostic scheme for detecting nodules in chest radiographs by means of massive training artificial neural network," *Acad Radiol*, vol. 12, pp. 191-201, Feb. 2005.
K. Suzuki, H. Abe, F. Li, and K. Doi, "Suppression of the contrast of ribs in chest radiographs by means of massive training artificial neural network," in *Proc. SPIE Medical Imaging (SPIE MI)*, San Diego, CA, 2004, pp. 1109-1119.
K. Suzuki, H. Abe, H. MacMahon, and K. Doi, "Image-processing technique for suppressing ribs in chest radiographs by means of massive training artificial neural network (MTANN)," *IEEE Trans Med Imaging*, vol. 25, pp. 406-416, Apr. 2006.
S. Oda, K. Awai, K. Suzuki, Y. Yanaga, Y. Funama, H. MacMahon, et al., "Performance of radiologists in detection of small pulmonary nodules on chest radiographs: effect of rib suppression with a massive-training artificial neural network," *AJR Am J Roentgenol*, vol. 193, pp. W397-W402, Nov. 2009.
K. Suzuki, F. Li, S. Sone, and K. Doi, "Computer-aided diagnostic scheme for distinction between benign and malignant nodules in thoracic low-dose CT by use of massive training artificial neural network," *IEEE Transactions on Medical Imaging*, vol. 24, pp. 1138-1150, Sep. 2005.
K. Suzuki, D. C. Rockey, and A. H. Dachman, "CT colonography: Advanced computer-aided detection scheme utilizing MTANNS for detection of "missed" polyps in a multicenter clinical trial," *Med Phys*, vol. 30, pp. 2-21, 2010.
K. Suzuki, H. Yoshida, J. Nappi, S. G. Armato, 3rd, and A. H. Dachman, "Mixture of expert 3D massive-training ANNs for reduction of multiple types of false positives in CAD for detection of polyps in CT colonography," *Med Phys*, vol. 35, pp. 694-703, Feb. 2008.
K. Suzuki, H. Yoshida, J. Nappi, and A. H. Dachman, "Massive-training artificial neural network (MTANN) for reduction of false positives in computer-aided detection of polyps: Suppression of rectal tubes," *Med Phys*, vol. 33, pp. 3814-3824, Oct. 2006.

(56) References Cited

OTHER PUBLICATIONS

J. Xu and K. Suzuki, "Massive-training support vector regression and Gaussian process for false-positive reduction in computer-aided detection of polyps in CT colonography," *Medical Physics*, vol. 38, pp. 1888-1902, 2011.

K. Suzuki, J. Zhang, and J. Xu, "Massive-training artificial neural network coupled with Laplacian-eigenfunction-based dimensionality reduction for computer-aided detection of polyps in CT colonography," *IEEE Trans Med Imaging*, vol. 29, pp. 1907-1917, Nov. 2010.

V. N. Vapnik, "Problem of Regression Estimation," in *Statistical Learning Theory*, ed New York: Wiley, 1998, pp. 26-28.

S. Haykin, "Statistical Nature of Learning Process," in *Neural Networks*, ed Upper Saddle River, NJ: Prentice Hall, 1998, pp. 84-87.

V. N. Vapnik, "SV Machine for Regression Estimation," in *Statistical Learning Theory*, ed New York: Wiley, 1998, pp. 549-558.

C. E. Rasmussen, "Gaussian processes for machine learning" 2006.

V. N. Vapnik, "Least Squares Method for Regression Estimation Problem," in *Statistical Learning Theory*, ed New York: Wiley, 1998, p. 34.

S. Haykin, "Back-Propagation Algorithm," in *Neural Networks*, ed Upper Saddle River, NJ: Prentice Hall, 1998, pp. 161-175.

J. Serra, *Image Analysis and Mathematical Morphology*. London: Academic Press, 1982.

C. Dorai and A. Jain, "COSMOS—A representation scheme for 3D free-form objects," *IEEE Transactions on Pattern Analysis and Machine Intelligence*, vol. 19, pp. 1115-1130, Oct. 1997.

J. Koenderink and A. Vandoorn, "Surface shape and curvature scales," *Image and Vision Computing*, vol. 10, pp. 557-564, Oct. 1992.

M. R. Banham and A. K. Katsaggelos, "Digital Image Restoration," *IEEE Signal Processing Magazine*, vol. 14, pp. 24-41, Mar. 1997.

J. C. Brailean, R. P. Kleihorst, S. Efstratiadis, A. K. Katsaggelos, and R. L. Lagendijk, "Noise reduction filters for dynamic image sequences: a review," *Proceedings of the IEEE*, vol. 83, pp. 1272-1292, 1995.

\* cited by examiner

11% of standard dose
Fig. 5(a)
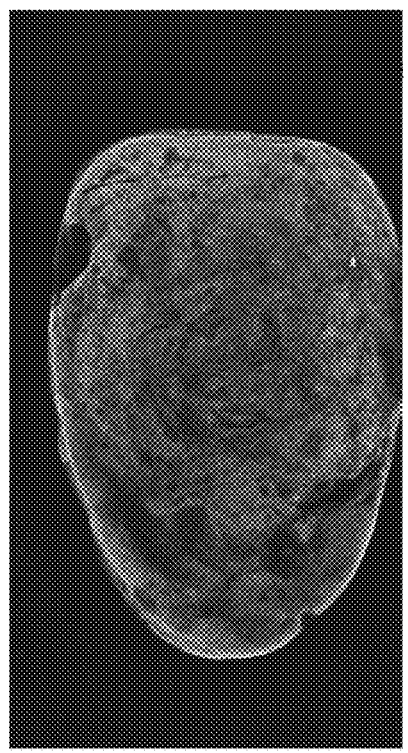
28% of standard dose
Fig. 5(b)
Standard dose
Fig. 5(c)
300% of standard dose
Fig. 5(d)
Figure 5 a) Input low-dose image (11%; SNR=2.6dB)  b) "Virtual" high-dose image (SNR=12.3dB)  c) "Gold-standard" real high-dose image (300%)

a) Input low-dose image (28%; SNR=8.6dB)  b) "Virtual" high-dose image (SNR=16.6dB)  c) "Gold-standard" real high-dose image (300%)

a) Input low-dose image (25%) with microcalcifications (indicated by arrows)

b) Microcalcification-extracted image a) Input low-dose image (25%)  b) "Virtual" standard-dose image  c) "Reference-standard" real standard-dose image (100%)

CONVERTING LOW-DOSE TO HIGHER DOSE MAMMOGRAPHIC IMAGES THROUGH MACHINE-LEARNING PROCESSES

FIELD

This patent specification relates generally to the field of mammography including full-field digital mammography and digitized screen-film mammography, and more particularly to methods, systems, and computer programs for converting lower-dose mammograms into higher-dose-like mammograms.

This patent specification also generally relates to computerized techniques for automated analysis of digital images, for example, as discussed in one or more of U.S. Pat. Nos. 5,751,787; 6,158,888; 7,412,024; 8,378,302; 8,395,120; 6,819,790; 6,754,380; and 7,545,965, and U.S. Publication No. 2006/0018524, all of which are hereby incorporated by reference.

This patent specification includes use of technologies referenced and discussed in the above-noted U.S. Patents and Applications, as well as those discussed in the documents identified in the following List of References, which are cited throughout the specification by reference number (as providing supporting information) and are hereby incorporated by reference:

LIST OF REFERENCES CITED IN TEXT

[1] S. A. Feig and R. E. Hendrick, "Radiation risk from screening mammography of women aged 40-49 years," *J Natl Cancer Inst Monogr*, pp. 119-24, 1997.

[2] U. S. P. S. T. Force, "Screening for breast cancer: recommendations and rationale," *Am Fam Physician*, vol. 65, pp. 2537-44, Jun. 15 2002.

[3] M. J. Yaffe and J. G. Mainprize, "Risk of radiation-induced breast cancer from mammographic screening," *Radiology*, vol. 258, pp. 98-105, January 2011.

[4] S. Obenauer, K. P. Hermann, and E. Grabbe, "Dose reduction in full-field digital mammography: an anthropomorphic breast phantom study," *Br J Radiol*, vol. 76, pp. 478-82, July 2003.

[5] R. L. Smathers, J. M. Boone, L. J. Lee, E. A. Berns, R. A. Miller, and A. M. Wright., "Radiation dose reduction for augmentation mammography," *AJR Am J Roentgenol*, vol. 188, pp. 1414-21, May 2007.

[6] X. Liu, C. J. Lai, G. J. Whitman, W. R. Geiser, Y. Shen, Y. Yi, et al., "Effects of exposure equalization on image signal-to-noise ratios in digital mammography: a simulation study with an anthropomorphic breast phantom," *Med Phys*, vol. 38, pp. 6489-501, December 2011.

[7] M. Yakabe, S. Sakai, H. Yabuuchi, Y. Matsuo, T. Kamitani, T. Setoguchi, et al., "Effect of dose reduction on the ability of digital mammography to detect simulated microcalcifications," *J Digit Imaging*, vol. 23, pp. 520-6, October 2010.

[8] W. Huda, K. M. Ogden, E. M. Scalzetti, D. R. Dance, and E. A. Bertrand, "How do lesion size and random noise affect detection performance in digital mammography?," *Acad Radiol*, vol. 13, pp. 1355-66, November 2006.

[9] A. S. Chawla, E. Samei, R. Saunders, C. Abbey, and D. Delong, "Effect of dose reduction on the detection of mammographic lesions: a mathematical observer model analysis," *Med Phys*, vol. 34, pp. 3385-98, August 2007.

[10] G. Gennaro, L. Katz, H. Souchay, C. Alberelli, and C. di Maggio, "Are phantoms useful for predicting the potential of dose reduction in full-field digital mammography?," *Phys Med Biol*, vol. 50, pp. 1851-70, Apr. 21 2005.

[11] N. T Ranger, J. Y. Lo, and E. Samei, "A technique optimization protocol and the potential for dose reduction in digital mammography," *Med Phys*, vol. 37, pp. 962-9, March 2010.

[12] E. Samei, R. S. Saunders, Jr., J. A. Baker, and D. M. Delong, "Digital mammography: effects of reduced radiation dose on diagnostic performance," *Radiology*, vol. 243, pp. 396-404, May 2007.

[13] K. C. Young, M. L. Ramsdale, and A. Rust, "Dose and image quality in mammography with an automatic beam quality system," *Br J Radiol*, vol. 69, pp. 555-62, June 1996.

[14] S. V. Destounis, P. DiNitto, W. Logan-Young, E. Bonaccio, M. L. Zuley, and K. M. Willison, "Can computer-aided detection with double reading of screening mammograms help decrease the false-negative rate?Initial experience," *Radiology*, vol. 232, pp. 578-84, August 2004.

[15] K. Suzuki, S. G. Armato, 3rd, F. Li, S. Sone, and K. Doi, "Massive training artificial neural network (MTANN) for reduction of false positives in computerized detection of lung nodules in low-dose computed tomography," *Med Phys*, vol. 30, pp. 1602-17, July 2003.

[16] K. Suzuki, I. Horiba, and N. Sugie, "Efficient approximation of neural filters for removing quantum noise from images," *IEEE Transactions on Signal Processing*, vol. 50, pp. 1787-1799, July 2002.

[17] K. Suzuki, I. Horiba, and N. Sugie, "Neural edge enhancer for supervised edge enhancement from noisy images," *IEEE Transactions on Pattern Analysis and Machine Intelligence*, vol. 25, pp. 1582-1596, December 2003.

[18] H. Arimura, S. Katsurgawa, K. Suzuki, F. Li, J. Shiraishi, S. Sone, et al., "Computerized scheme for automated detection of lung nodules in low-dose computed tomography images for lung cancer screening," *Academic Radiology*, vol. 11, pp. 617-629, June 2004.

[19] F. Li, H. Arimura, K. Suzuki, J. Shiraishi, Q. Li. H. Abe, et al., "Computer-aided detection of peripheral lung cancers missed at CT: ROC analyses without and with localization," *Radiology*, vol. 237, pp. 684-90, November 2005.

[20] K. Suzuki, J. Shiraishi, H. Abe, H. MacMahon, and K. Doi, "False-positive reduction in computer-aided diagnostic scheme for detecting nodules in chest radiographs by means of massive training artificial neural network," *Acad Radiol*, vol. 12, pp. 191-201, February 2005.

[21] K. Suzuki, H. Abe, F. Li, and K. Doi, "Suppression of the contrast of ribs in chest radiographs by means of massive training artificial neural network," in *Proc. SPIE Medical Imaging (SPIE MI)*, San Diego, Calif., 2004, pp. 1109-1119.

[22] K. Suzuki, H. Abe, H. MacMahon, and K. Doi, "Image-processing technique for suppressing ribs in chest radiographs by means of massive training artificial neural network (MTANN)," *IEEE Trans Med Imaging*, vol. 25, pp. 406-16, April 2006.

[23] S. Oda, K. Awai, K. Suzuki, Y. Yanaga, Y. Funama, H. MacMahon, et al., "Performance of radiologists in detection of small pulmonary nodules on chest radiographs: effect of rib suppression with a massive-training artificial neural network," *AJR Am J Roentgenol*, vol. 193, pp. W397-402, November 2009.

[24] K. Suzuki, F. Li, S. Sone, and K. Doi, "Computer-aided diagnostic scheme for distinction between benign and malignant nodules in thoracic low-dose CT by use of massive training artificial neural network," *IEEE Transactions on Medical Imaging*, vol. 24, pp. 1138-1150, September 2005.

[25] K. Suzuki, D. C. Rockey, and A, H. Dachman, "CT colonography: Advanced computer-aided detection scheme utilizing MTANNs for detection of "missed" polyps in a multicenter clinical trial," *Med Phys*, vol. 30, pp. 2-21, 2010.

[26] K. Suzuki, H. Yoshida, J. Nappi, S. G. Armato, 3rd, and A. H. Dachman, "Mixture of expert 3D massive-training ANNs for reduction of multiple types of false positives in CAD for detection of polyps in CT colonography," *Med Phys*, vol. 35, pp. 694-703, February 2008.

[27] K. Suzuki, H. Yoshida, J. Nappi, and A. H. Dachman, "Massive-training artificial neural network (MTANN) for reduction of false positives in computer-aided detection of polyps: Suppression of rectal tubes," *Med Phys*, vol. 33, pp. 3814-24, October 2006.

[28] J. Xu and K. Suzuki, "Massive-training support vector regression and Gaussian process for false-positive reduction in computer-aided detection of polyps in CT colonography," *Medical Physics*, vol. 38, pp. 1888-1902, 2011.

[29] K. Suzuki, J. Zhang, and J. Xu, "Massive-training artificial neural network coupled with Laplacian-eigenfunction-based dimensionality reduction for computer-aided detection of polyps in CT colonography," *IEEE Trans Med Imaging*. vol. 29, pp. 1907-17, November 2010.

[30] V. N. Vapnik, "Problem of Regression Estimation," in *Statistical Learning Theory*, ed New York: Wiley, 1998, pp. 26-28.

[31] S. Haykin, "Statistical Nature of Learning Process," in *Neural Networks*, ed Upper Saddle River, N.J.: Prentice Hall, 1998, pp. 84-87.

[32] V. N. Vapnik, "SV Machine for Regression Estimation," in *Statistical Learning Theory*, ed New York: Wiley, 1998, pp. 549-558.

[33] C. E. Rasmussen, "Gaussian processes for machine learning," 2006.

[34] V. N. Vapnik, "Least Squares Method for Regression Estimation Problem," in *Statistical Learning Theory*, ed New York: Wiley, 1998, p. 34.

[35] S. Haykin, "Back-Propagation Algorithm," in *Neural Networks*, ed Upper Saddle River, N.J.: Prentice Hall, 1998, pp. 161-175.

[36] J. Serra, Image Analysis and Mathematical Morphology. London: Academic Press, 1982.

[37] C. Dorai and A. Jain, "COSMOS—A representation scheme for 3D free-form objects," *IEEE Transactions on Pattern Analysis and Machine Intelligence*, vol. 19, pp. 1115-1130, October 1997.

[38] J. Koenderink and A. Vandoorn, "Surface shape and curvature scales," *Image and Vision Computing*, vol. 10, pp. 557-564, October 1992.

[39] M. R. Banham and A. K. Katsaggelos, "Digital Image Restoration," *IEEE Signal Processing Magazine*, vol. 14, pp. 24-41, March 1997.

[40] J. C. Brailean, R. P. Kleihorst, S. Efstratiadis, A. K. Katsaggelos, and R. L. Lagendijk, "Noise reduction filters for dynamic image sequences: a review," *Proceedings of the IEEE*, vol. 83, pp. 1272-1292, 1995.

BACKGROUND

Mammography has been used in screening of breast cancer. The goal of screening mammography is the early detection of breast cancer through detection of masses and/or microcalcifications. Mammograms use doses of ionizing radiation usually at a lower-energy X-ray level (usually around 30 kVp).

The U.S. Preventive Services Task Force (USPSTF) recommended in 2009 screening of women aged between 50 and 74 with mammography every two years. The Canadian Task Force on Preventive Health Care and the European Cancer Observatory recommends mammography every 2-3 years between 50 and 69.

The radiation exposure associated with mammography is a potential risk of screening. The risk of exposure appears to be greater in younger women. The largest study of radiation risk from mammography concluded that for women 40 years of age or older, the risk of radiation-induced breast cancer was acceptable, particularly compared with the potential benefit of mammographic screening, with a benefit-to-risk ratio of 48.5 lives saved for each life lost due to radiation exposure 11. Organizations such as the National Cancer Institute and USPSTF take such risks into account when formulating screening guidelines [2].

However, a study by Yaffe and Mainprize [3] predicted that there would be 86 cancers induced and 11 deaths due to radiation-induced breast cancer among a cohort of 100,000 women each receiving a dose of 3.7 mGy to both breasts and who were screened annually from age 40 to 55 years and biennially thereafter to age 74 years.

The majority of health experts agree that the risk of breast cancer for asymptomatic women under 35 is not high enough to warrant the risk of radiation exposure. For this reason, and because the radiation sensitivity of the breast in women under 35 is possibly greater than in older women, most radiologists will not perform screening mammography in women under 40.

When a radiologist or a computer detects, interprets, analyzes, and diagnoses mammograms, there is a tradeoff between radiation dose levels and image quality. Higher radiation doses result in higher signal-to-noise ratio, while lower doses lead to increased image noise including quantum noise and electronic noise. The higher radiation would increase the risk of radiation-induced cancer. Therefore, it is important to reduce radiation exposures and doses as much as possible, or radiation exposures and doses should be kept as low as reasonably achievable.

Researchers have studied radiation dose reduction in mammography. S. Obenauer et al. [4] compared full-field digital mammography with screen-film mammography, and investigated a potential of dose reduction with an anthropomorphic breast phantom by changing anode-filter combinations in full-field digital mammography. R. L. Smathers et al. [5] evaluated the effects of anode-filter combinations on radiation dose reduction in mammography with 206 clinical cases. They showed that changing anode-filter combinations could reduce radiation dose by 35%. X. Liu et al. [6] investigated the effects of exposure equalization on the image quality and radiation dose reduction with an anthropomorphic breast phantom. They showed that the expose equalization technique could reduce radiation dose by 34%. M. Yakabe et al. [7] investigated the relationship between radiation dose and the detectability of simulated microcalcifications with an anthropomorphic breast phantom. The radiation dose was changed by changing tube-current-time-product, mAs. W. Huda et al. [8] investigated the effects of random noise and lesion size on the detection performance by radiologists with an anthropomorphic breast phantom. A. S. Chawla et al. [9] investigated the effect of radiation dose reduction on the detection of breast lesions with simulated noise by using mathematical observer model analysis. G. Gennaro et al. [10] evaluated the phantom use in radiation dose reduction in mammography. N. T. Ranger et al. [11] investigated optimization of tube voltage, kVp and anode-filter combinations in mammography. E. Samei et al. [12] assessed the relationship between radiation dose and observer accuracy in the detection of simulated lesions in mammography. K. C. Young et al. [13] assessed the automatic beam quality selection function of a vendor's mammography system.

On the other hand, computer-aided diagnostic (CAD) systems are being tested to decrease the number of cases of cancer that are missed in mammograms. In one test, a computer identified 71% of the cases of cancer that had been missed by physicians. However, the computer also flagged twice as many non-cancerous masses than the physicians did. In a second study of a larger set of mammograms, a computer recommended six biopsies that physicians did not. All six turned out to be cancers that would have been missed [14].

In the field of CAD, K. Suzuki et al. developed a pixel-based machine-learning technique based on an artificial neural network (ANN), called massive-training ANNs (MTANN), for distinguishing a specific opacity (pattern) from other opacities (patterns) in 2D CT images [15]. An MTANN was developed by extension of neural filters [16] and a neural edge enhancer [17] to accommodate various pattern-recognition and classification tasks [15]. The 2D MTANN was applied to reduction of false positives (FPs) in computerized detection of lung nodules on 2D CT slices in a slice-by-slice way [15, 18, 19] and in chest radiographs [20], the separation of ribs from soft tissue in chest radiographs [21-23], and the distinction between benign and malignant lung nodules on 2D CT slices [24]. For processing of three-dimensional (3D) volume data, a 3D MTANN was developed by extending the structure of the 2D MTANN, and it was applied to 3D CT colonography data [25-29].

SUMMARY OF THE DISCLOSURE

This patent specification describes converting low-dose mammographic images with much noise into higher quality, less noise, higher-dose-like mammographic images. The described method and system use a trainable nonlinear regession (TNR) model with a patch-input-pixel-output scheme, which can be called pixel-based TNR (PTNR). In a preferred example, an image patch is extracted from an input mammogram acquired at a reduced x-ray radiation dose (lower-dose), and pixel values in the patch are entered into the PTNR as input. The output of the PTNR is a smaller patch, preferably a single pixel, that corresponds to the center pixel of the input image patch. The PTNR receives such patches, for example a respective patch for each pixel of the input image in a raster or some other pattern. The PTNR is trained with matched pairs of mammograms, inputting low-dose mammograms together with corresponding desired x-ray radiation dose mammograms (higher-dose), such as standard dose mammograms, which are ideal images for the output images. Through the training, the PTNR learns to convert low-dose mammograms to high-dose-like mammograms. Once trained, the trained PTNR does not require the higher-dose mammograms anymore. When a new reduced x-ray radiation dose (low dose) mammogram is entered, the trained PTNR would output a pixel value similar to its desired pixel value, in other words, it would output high-dose-like mammograms or "virtual high-dose" mammograms where noise and artifacts due to low radiation dose are substantially reduced, i.e., a higher image quality. With the "virtual high-dose" mammograms, the detectability of lesions and clinically important findings such as masses and microcalcifications can be improved. This patent specification further describes a computer program product that stores in computer-readable media, in non-transitory form, instructions that when loaded into and executed by a computer system carry out the processes described herein.

BRIEF DESCRIPTION OF THE DRAWINGS

FIGS. 2A' and 2B' show a detailed architecture and designing of a modified PTNR, respectively.

FIG. 5(a) shows a mammogram of a ham phantom at 11% of a standard dose. It is the input image used for training of a PTNR labeled PTNR 11.

FIG. 5(b) shows a mammogram of the ham phantom at 28% of the standard dose. It is the input image used for training of a PTNR labeled PTNR28.

FIG. 5(c) shows a mammogram of the ham phantom at the standard dose.

FIG. 5(d) shows the desired image used for training of PTNR11 and PTNR28.

DETAILED DESCRIPTION

Figure 1A:
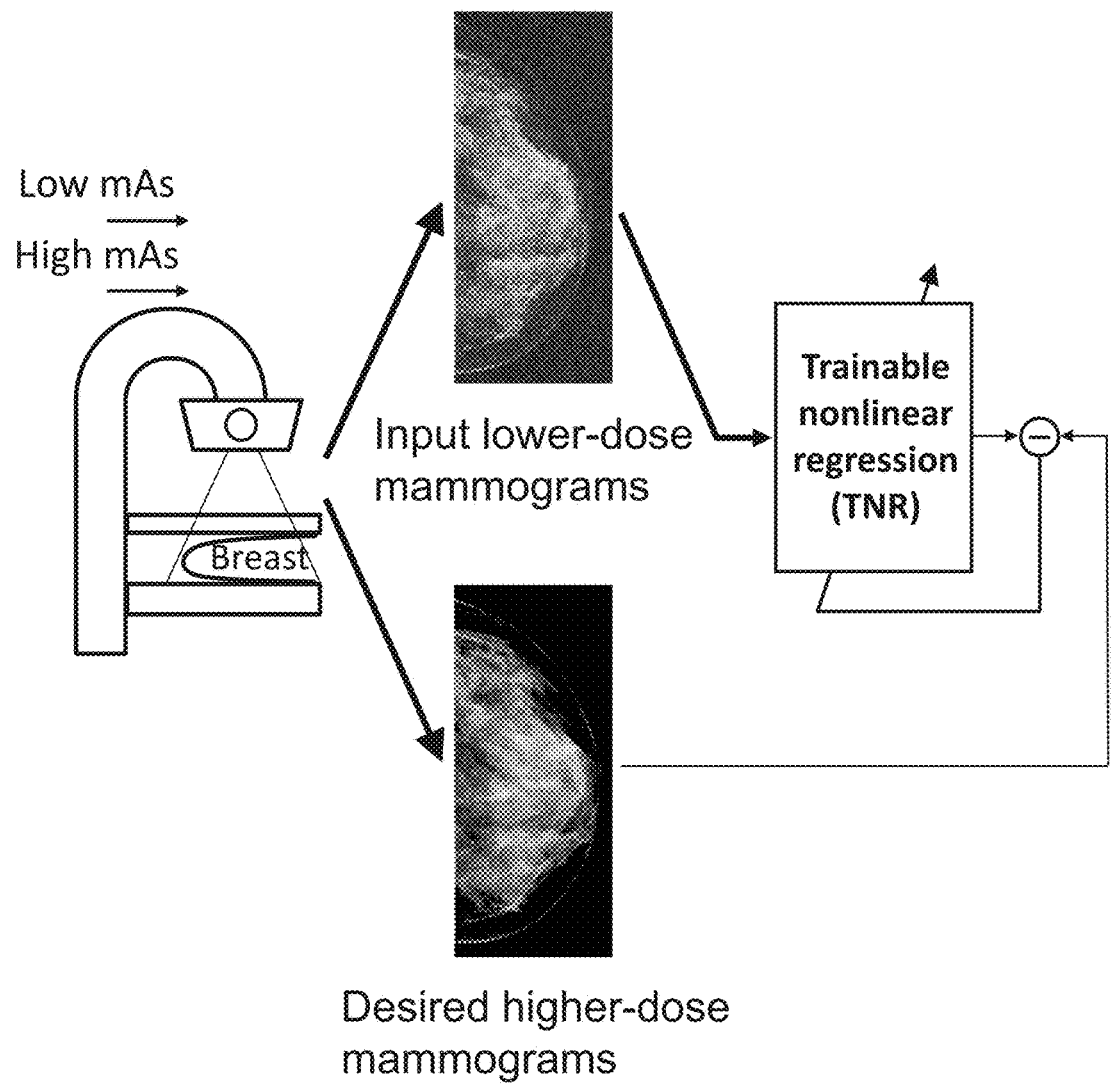
FIG. 1A shows a schematic diagram of a PTNR in a design step.

In preferred examples, pixel-based trainable nonlinear regression (PTNR) converts lower-dose mammograms to higher-quality, higher-dose-like mammograms. Lower-dose mammograms are of lower image quality with much noise. Higher-dose-like mammograms look like real, high-dose mammograms that are of higher image quality with less noise or artifacts. The PTNR uses a trainable nonlinear regression (TNR) model that processes pixels in mammograms. There are two main steps associated with PTNR: (1) a design step to determine the parameters in PTNR by using designing images and (2) a conversion step to convert low-dose mammograms to higher-dose-like mammograms or "virtual high-dose" mammograms where noise and artifacts are eliminated or at least substantially reduced. FIG. 1A shows a schematic diagram of a PTNR in a design step. In the design step, the PTNR is designed with input lower-dose mammograms with much noise and the corresponding desired higher-dose mammograms with less noise or artifact. For example, as illustrated in FIG. 1A, a breast imaging structure comprises an x-ray source emitting an imaging x-ray beam that passes through a breast compressed between a compression paddle and a breast platform covering a 2D image receptor. The structure can operate in a low-mAs mode to produce low-dose, lower image quality mammograms, or an a high-mAs mode to produce higher-dose, higher image quality mammograms, such as mammograms taken at the dose recommended by the current Mammogram Quality Standards Act (MQSA) for standard screening mammograms (e.g., 3.7-4.2 mGy average mean glandular radiation dose for 2-view mammograms of a patient's breasts) or at higher dose. The parameters in the TNR are adjusted to minimizing the difference between the output images and the corresponding desired mammograms. Through the designing process, the PTNR learns to convert lower-dose mammograms being lower-image-quality with much noise to higher-dose-like mammograms being higher-image-quality with less noise or artifact.

The number of designing input and desired mammograms may be relatively small, e.g., 1, 10, or 100 or less. However, a larger number of designing images may be used as well, e.g., 100-1,000 mammograms, 1,000-10,000 mammograms, or more than 10,000 mammograms.

Figure 1B:
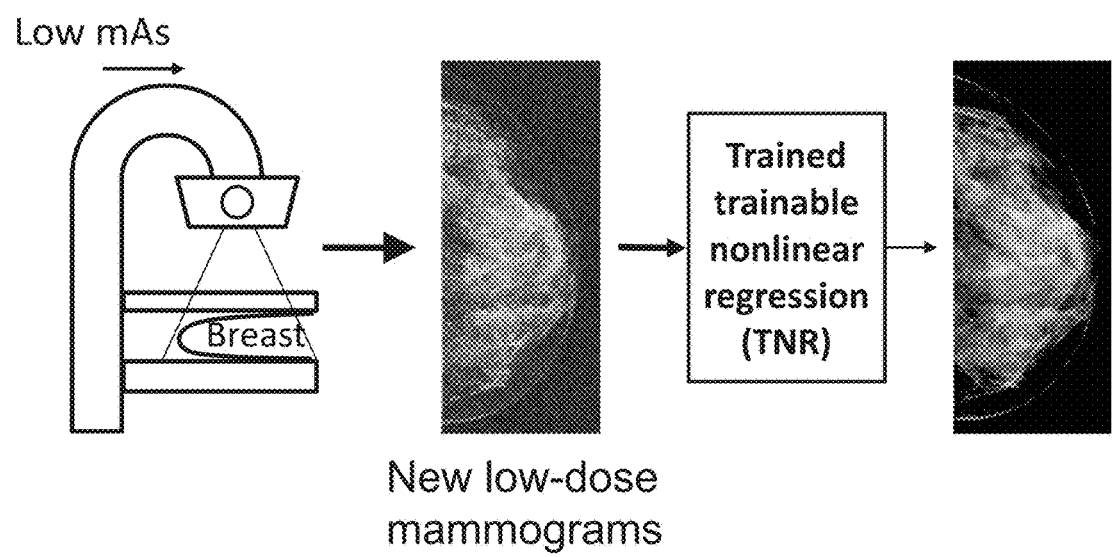
FIG. 1B shows a schematic diagram of a PTNR in a conversion step.

FIG. 1B shows a schematic diagram of a PTNR in a conversion step. Once the PTNR is trained, the trained PTNR does not require higher-dose mammograms anymore. When a new reduced radiation dose (low dose) mammogram is entered, the trained PTNR would output an image similar to its desired image, in other words, it would output high-dose-like high-quality mammograms or "virtual high-dose" mammograms where noise and artifacts due to low radiation dose are substantially reduced. The noise in low-dose mammograms contains two different types of noise: quantum noise and electronic noise. Quantum noise is modeled as signal-dependent noise, and electronic noise is modeled as signal-independent noise. The PTNR is expected to eliminate or at least substantially reduce both quantum noise and electronic noise. In addition to noise characteristics, the conspicuity of breast tissue such as masses (or tumors), architectural distortion (early sign of breast cancer), milk ducts, and breast cancer including ductal carcinoma in situ, and microcalcifications in higher-dose mammograms is higher than that of such objects in lower-dose mammograms. Therefore, the PTNR is expected to improve the conspicuity of such normal and abnormal structures in mammograms. With improved mammograms provided by the PTNR, radiologists' diagnostic performance, namely, regarding sensitivity and specificity of lesions would be improved; and thus, parameters regarding mortality and incidence of breast cancer as well as other breast diseases would potentially be improved with the PTNR-converted mammograms.

Figure 2A:
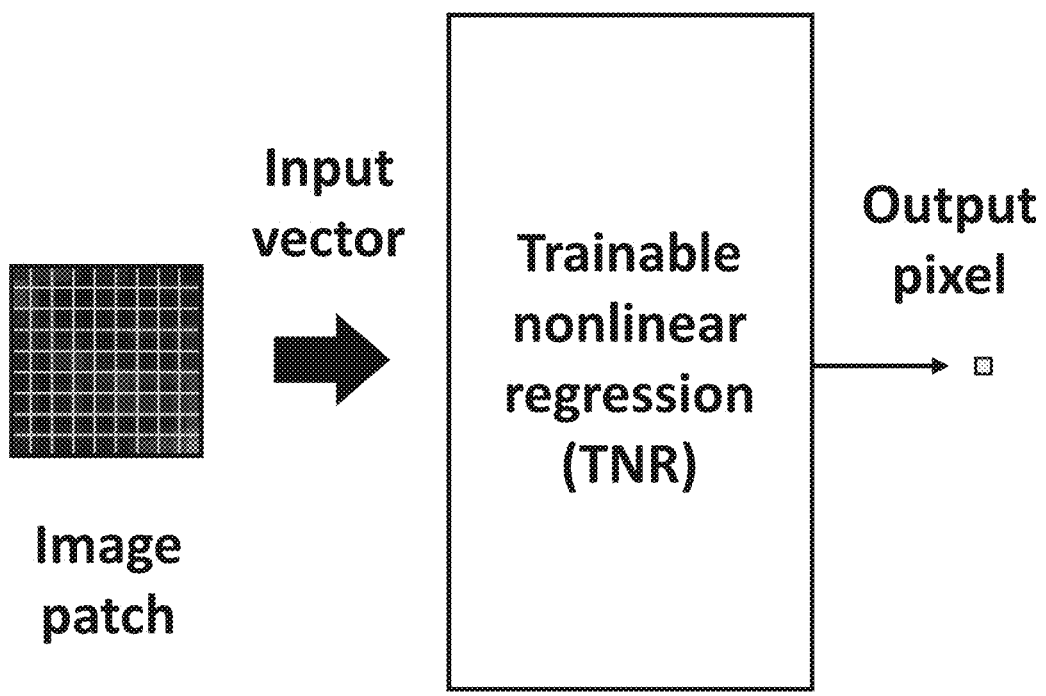
FIG. 2A shows a detailed architecture of a PTNR that uses a trainable nonlinear regression (TNR) model with a patch-input-pixel-output scheme.

FIG. 2A shows an example of a detailed architecture of a PTNR that uses a trainable nonlinear regression (TNR) model, the formulation of which is described in [30], with a patch-input-pixel-output scheme. See, for example pages 26-28 in [30]. The TNR may be a regression model such as an artificial neural network regression model, the formulation of which is descried in [31]), (see, for example pages 84-87 in [31]), a support vector regression model, the formulation and theory of which is descried in [32](see, for example pages 549-558 in [32]), and a nonlinear Gaussian process regression model, the formulation and theory of which is descried in [33]. Other regression models or machine-learning models may be used such as a nearest neighbor algorithm, association rule learning, inductive logic programming, reinforcement learning, representation learning, similarity learning, sparse dictionary learning, manifold learning, dictionary learning, boosting, Bayesian networks, case-based reasoning, Kernel machines, subspace learning, Naive Bayes classifiers, ensemble learning, random forest, decision trees, and statistical relational learning. Among the above models, classifier models such as Naive Bayes classifiers, Bayesian networks, random forest, and decision trees can be used in the PTNR, but the performance of the PTNR may not as high as the use of a regression model. In a preferred PTNR process, first an image patch is extracted from an input mammogram that is acquired at a reduced x-ray radiation dose (lower dose). Pixel values in the image patch are entered into the TNR as input. The output of the PTNR in this example preferably is a single pixel O(x,y) that corresponds to the center pixel in the input image patch, represented by $$O(x,y)=\text{TNR}\{I(x,y)\}, \quad (1)$$

$$I(x,y)=\{g(x-i,y-j)|i,j \in P\}, \quad (2)$$

where TNR is a trainable regression model, I(x,y) is the input vector, x and y are the image coordinates, g(x,y) is an input mammogram, P is an image patch, and i and j are variables.

To locate the center of the image patch accurately, the size of the image patch is preferably an odd number. Thus, the size of the image patch may be 3×3, 5×5, 7×7, 9×9, 11×11, 13×13, 15×15 pixels or larger. However, the size of the image patch can be an even number, such as 2×2, 4×4, and 5×5 pixels. The image patch preferably is a square but other array shapes can be used, such as rectangular or rounded. To obtain an entire output image, each pixel in the output pixel is converted by using the PTNR. Converted pixels outputted from the TNR are arranged and put into the corresponding pixel positions in the output image, which forms an output "virtual high-dose" mammogram.

Figure 2B:
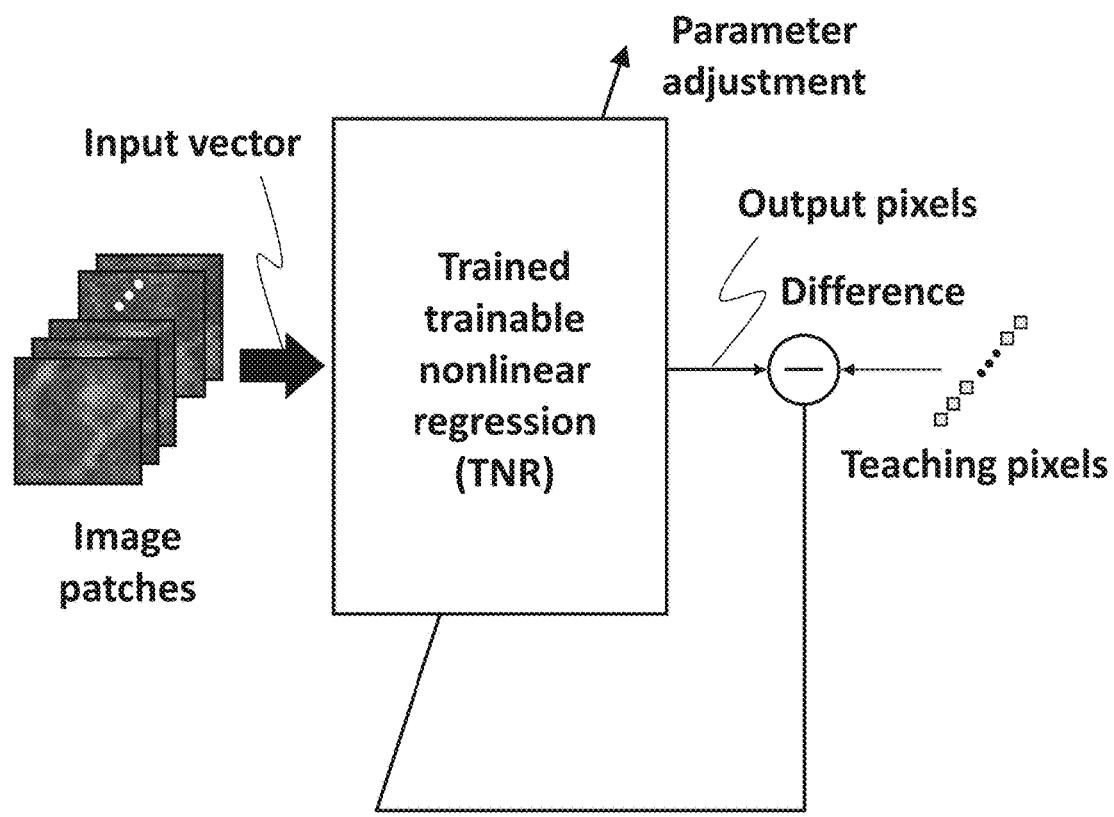
FIG. 2B shows designing of a PTNR.
Figure 2A:
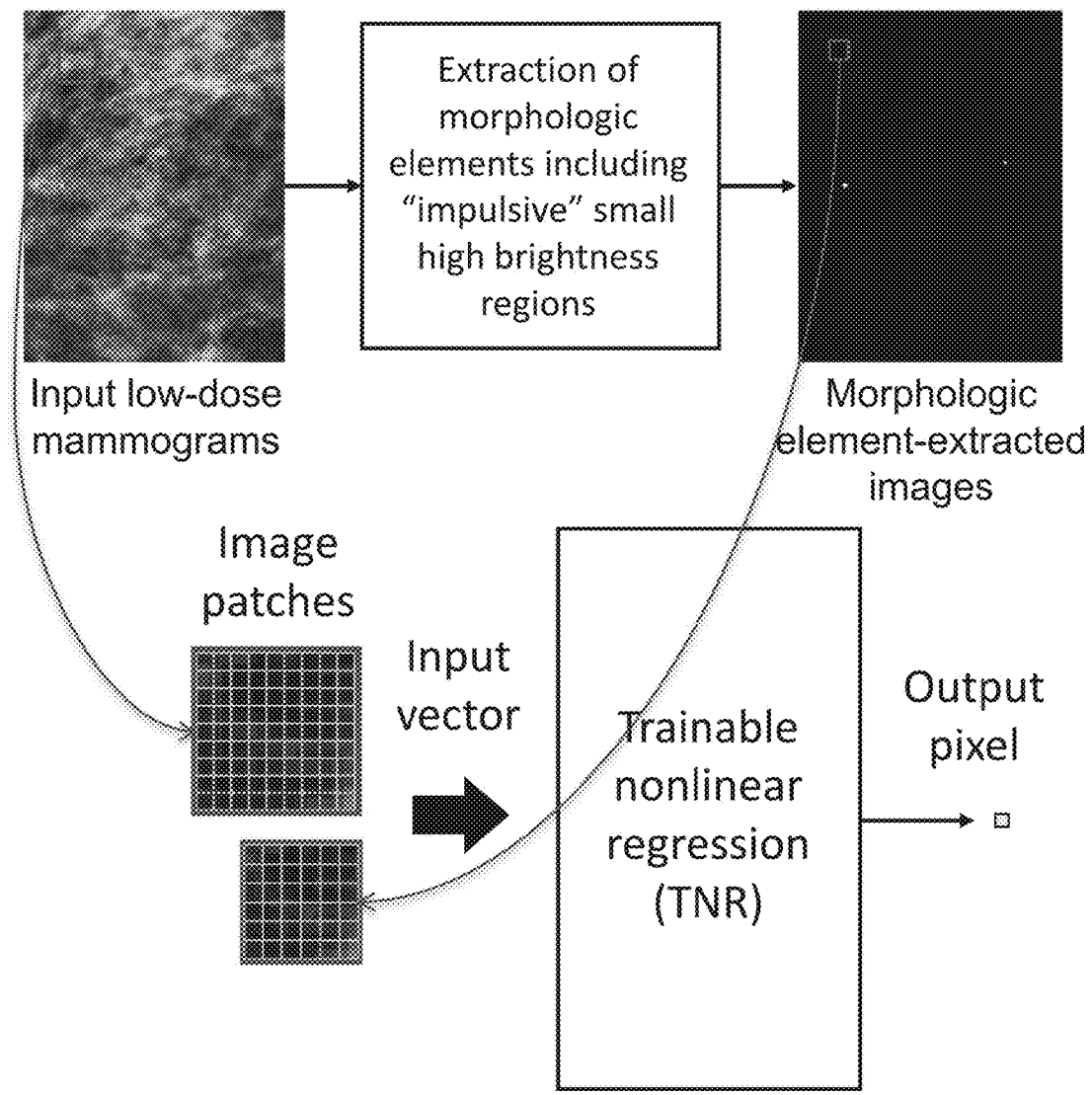
Figure 2B:
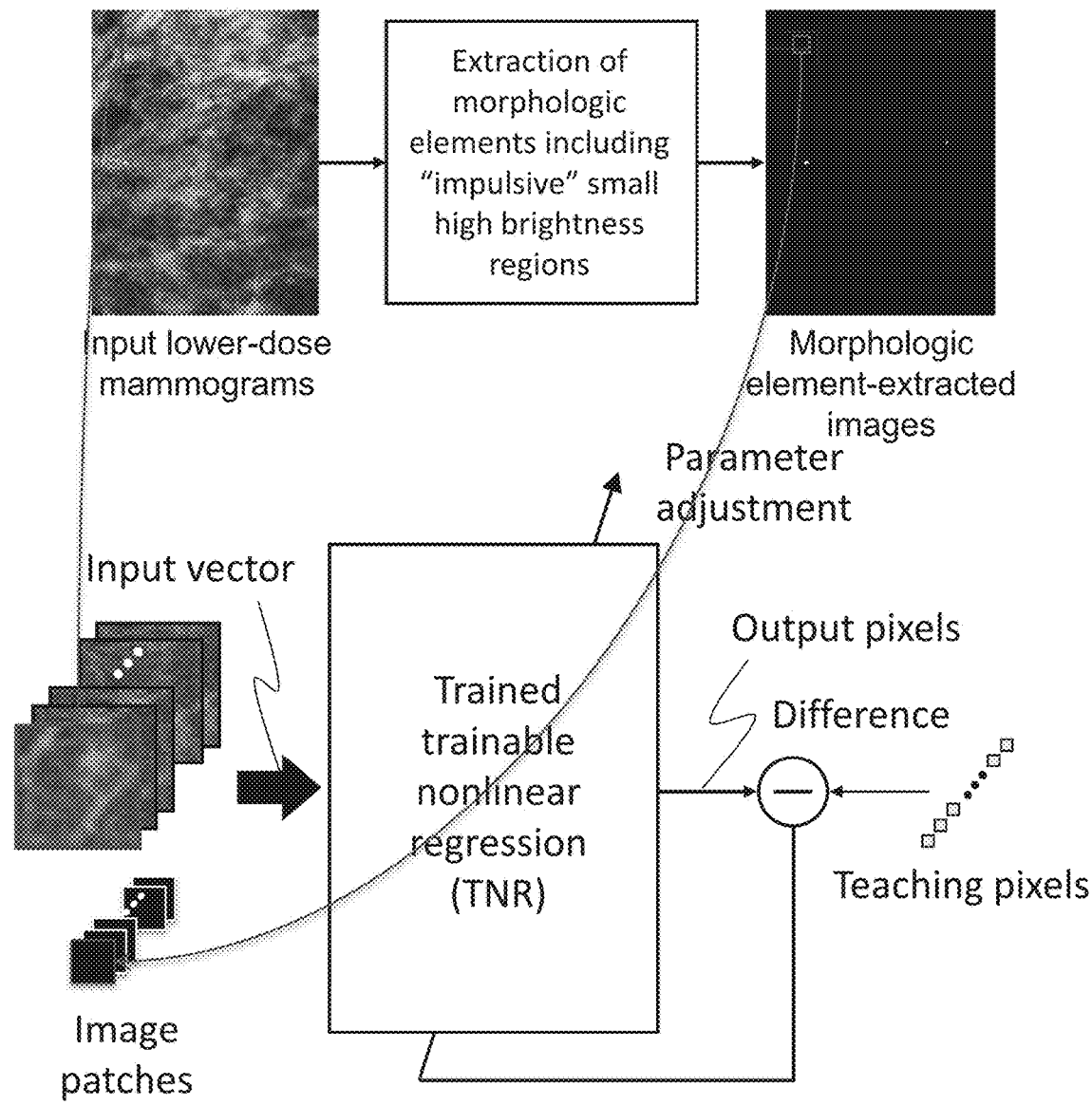

FIG. 2B shows designing of a PTNR. First, a large number of image patches together with the corresponding desired pixel values are acquired from the input lower-dose mammograms and desired higher-dose mammograms, respectively. Input vectors are calculated from the image patches. The input vectors are then entered to the TNR model as input. Output pixel values from the TNR are calculated based on the current parameters in the model. Then, the output pixel values are compared with the corresponding desired pixel values in the desired mammograms, and the difference "d" between the two is calculated, for example, represented by $$d = \sum_p \{D^{(p)} - O^{(p)}\}^2, \quad (3)$$

where D is the p-th pixel value in the desired output image, and O is the p-th pixel value in the output mammogram.

The parameters in the TNR model are adjusted so as to minimize or at least reduce the difference. A method to minimize the difference between the output and the desired value under the least square criterion [34] may be used to adjust the TNR model. See, for example page 34 in [34]. The difference calculation and the adjustment are repeated. As the adjustment proceeds, the output pixel values and thus the output images become closer to the corresponding desired higher-dose mammograms. When a stopping condition is fulfilled, the adjustment process is stopped. The stopping condition may be set as, for example, (a) an average difference is smaller than a predetermined difference, or (b) the number of adjustments is greater than a predetermined number of adjustments. After training, the PTNR would output "virtual high-dose" mammograms where noise and artifacts due to low radiation dose are substantially reduced. With the higher-quality "virtual high-dose" mammograms, the detectability of lesions and clinically important findings such as masses and microcalcifications can be improved.

FIG. 2A' shows an example of a detailed architecture of a modified PTNR. An extractor for morphologic elements including "impulsive" small high brightness regions is added to the basic PTNR. Low-dose mammograms are entered to the extractor to obtain images that extract or enhance morphologic elements including "impulsive" small high brightness regions. The "impulsive" small high brightness regions may be microcalcifications. Thus, one kind of the output images of the extractor may be considered as microcalcification-extracted images. Image patches are extracted from both original low-dose mammograms and morphologic-elements-extracted images, where the image patches extracted from the original low-dose mammograms may be larger or equal to those extracted from morphologic-elements-extracted images. The size of the image patches extracted from the morphologic-elements-extracted images may be as small as one single pixel. The extracted image patches form an input vector to the TNR.

FIG. 2B' shows designing of the modified PTNR. Image patches extracted from both original low-dose mammograms and morphologic-elements-extracted images form an input vector to the TNR. Output pixels are calculated based on the input vector, and parameters are adjusted to minimize the difference between the output pixels and the corresponding teaching pixels.

Figure 3A:
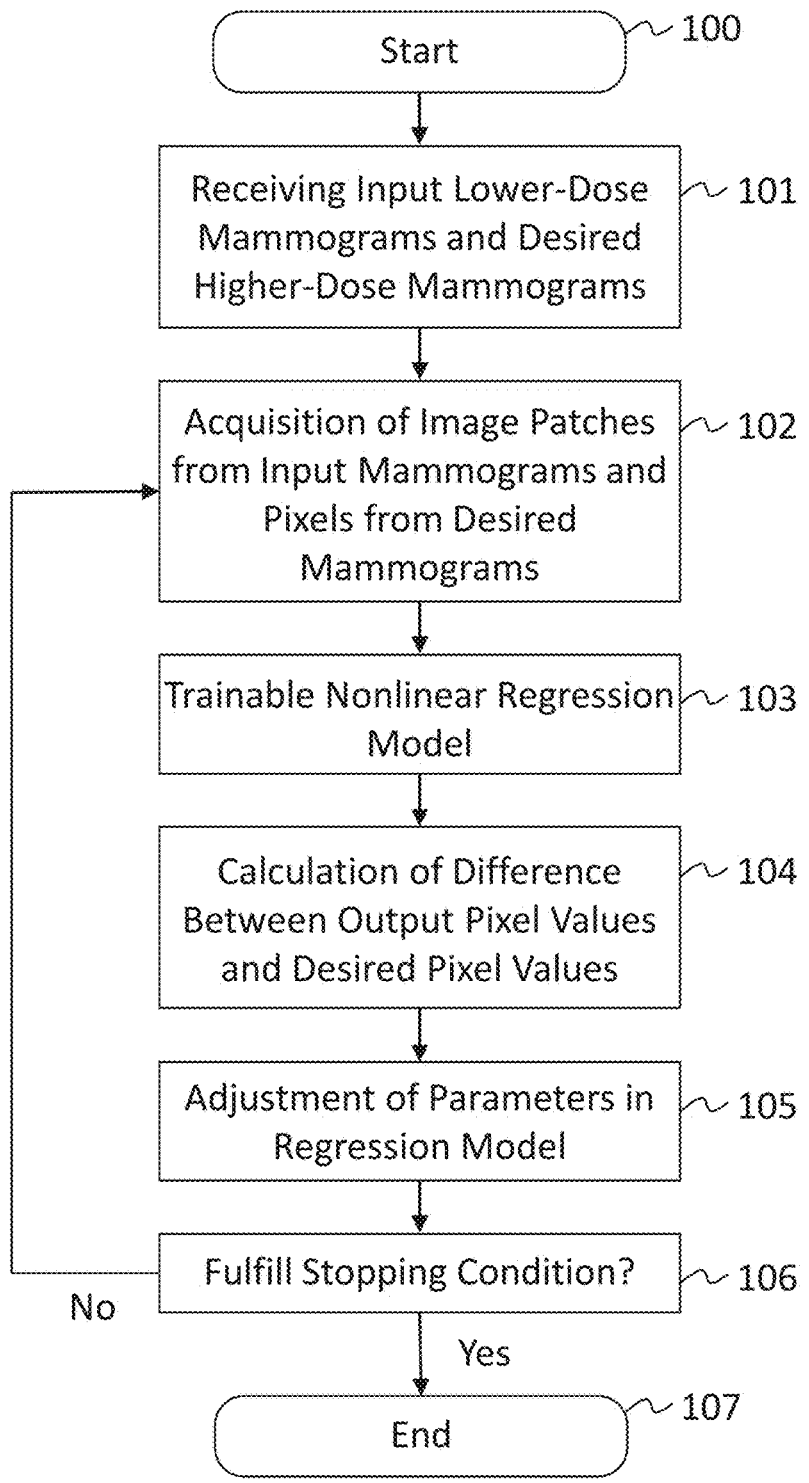
FIG. 3A shows a flow chart for a design step of a PTNR.

FIG. 3A shows a flow chart for a design step of a PTNR. First, in step 101, the PTNR receives input lower-dose mammograms with much noise and the corresponding desired higher-dose mammograms with less noise or artifact, which are ideal or desired images to the input lower-dose mammograms. In other words, the input mammograms are of lower image quality, and the desired mammograms are of higher image quality. In step 102, image patches are acquired from the input mammograms, and the corresponding pixels are acquired from the desired mammograms. Typically, a desired pixel corresponds to the center of an image patch. For example, when an image patch has 3×3 pixels, the corresponding location of the desired pixel is located at the second row and the second column in the image patch. In step 103, pixel values in the image patch form an N-dimensional input vector where N is the number of pixels in the image patch. The N-dimensional input vector is entered to the TNR model as input. The TNR may be a regression model such as an artificial neural network regression model or some other practical regression model. Given the input vector, the TNR with the current set of parameters outputs some output value. In step 104, a difference between the output pixel value and its desired pixel value obtained from the desired mammogram is calculated. The difference may be defined as a mean absolute error, a mean squared error, a Mahalanobis distance measure, and similarity measures such as mutual information. In step 105, parameters in the TNR are adjusted so as to minimize or at least reduce the difference. The adjustment may be made by using an optimization algorithm such as the steepest descent method or Newton's method. When an artificial neural network regression model is used as the regression model in the TNR, the error-back propagation algorithm [35] can be used to adjust the parameters in the model, i.e., weights between layers in the artificial neural network regression model. The error-back propagation algorithm is an example of the method for adjusting the parameters in the artificial neural network regression model. The formulation and derivation of the error-back propagation algorithm are described in [35] in detail. See, for example pages 161-175 in [35]. In step 106, when a predetermined stopping condition is met, the training is stopped; otherwise it goes back to step 102. The stopping condition may be set as, for example, (a) the average difference is smaller than a predetermined difference, or (b) the number of adjustments is greater than a predetermined number of adjustments.

Figure 3B:
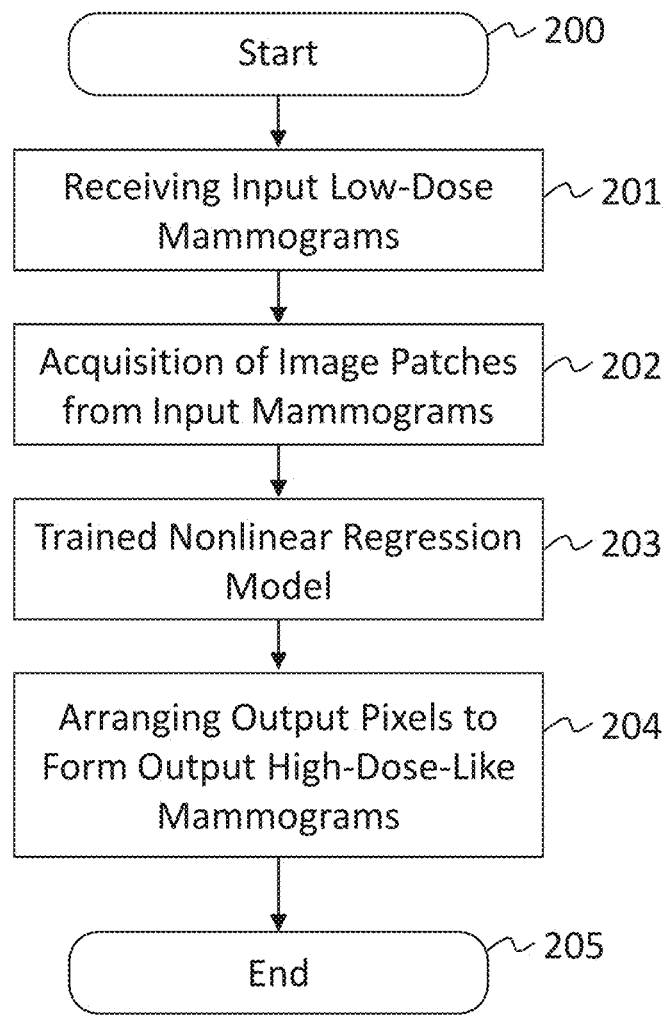
FIG. 3B shows a flow chart of a conversion step of a PTNR.

FIG. 3B shows a flow chart of a conversion step of a PTNR. This step is performed after the design step in FIG. 3A. First, in step 201, the designed PTNR receives input low-dose mammograms with much noise. In step 202, image patches are acquired from input low-dose mammograms that are different from the lower-dose marmnograms used in the design step. In step 203, N dimensional input vectors comprising pixel values in the image patches are entered to the trained TNR as input, and the trained TNR outputs output pixels. In step 205, the output pixels are arranged and put to the corresponding locations in the output image to form a high-dose-like mammogram or a "virtual high-dose" mammogram where noise and artifacts due to low radiation dose are reduced substantially. Thus, the designed PTNR provides high-quality "virtual high-dose" mammograms.

Figures 4A, 4B:
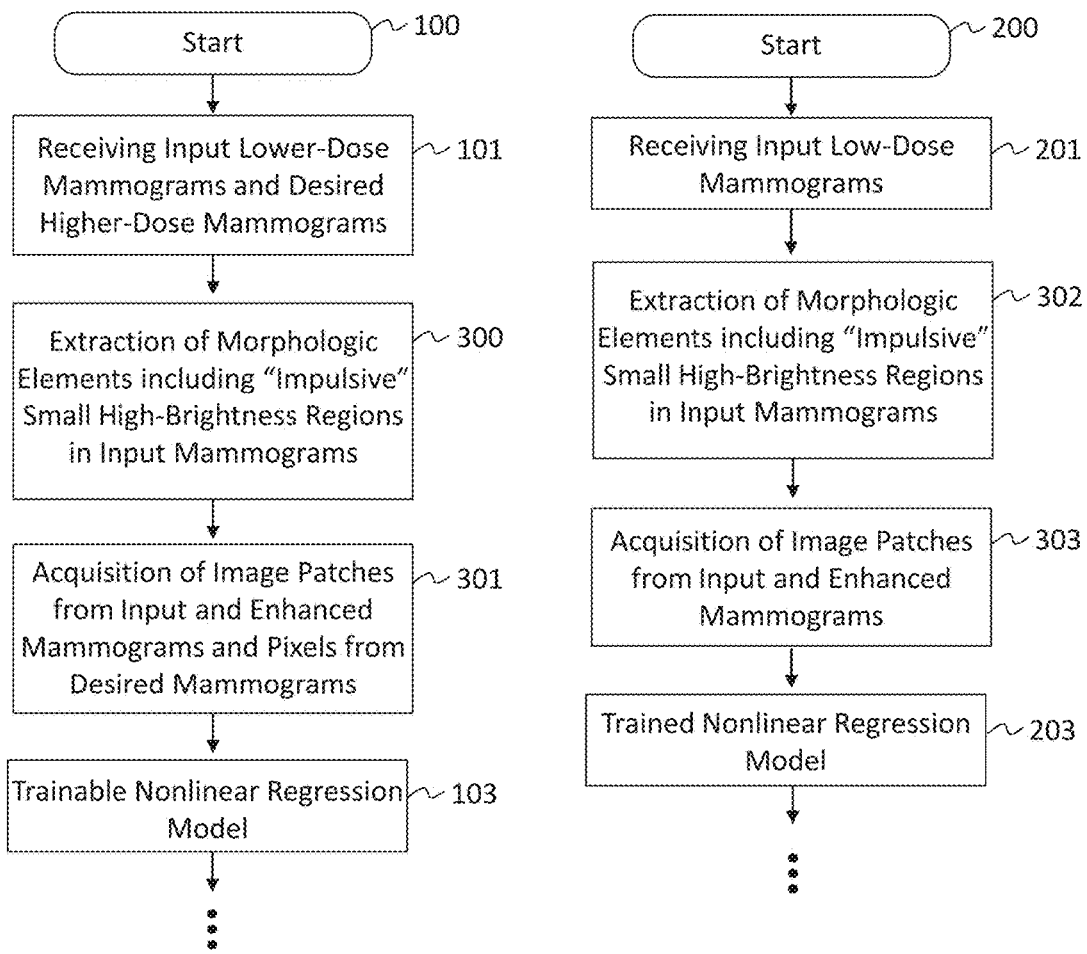
FIGS. 4A and 4B show flow charts for a design step and a conversion step of a modified PTNR, respectively.

FIGS. 4A and 4B show flow charts for a modified PTNR. A new step 300 is inserted between steps 101 and 102 in the design step of the PTNR in FIG. 3A; and a new step 301 is inserted between steps 201 and 202 in the conversion step of the PTNR in FIG. 3B. In step 300, morphologic elements including "impulsive" small high brightness regions in the input lower-dose mammograms that are received in step 101 are enhanced by using mathematical morphologic filtering [36] and a median-filter-based method (described far below in this paragraph). This step aims to enhance or extract clinically important structures in mammograms such as breast tissue, masses (or tumors), architectural distortion (early sign of breast cancer), milk ducts, and breast cancer including ductal carcinoma in situ, and microcalcifications. Morphologic elements may represent such breast tissue patterns. The "impulsive" small high-brightness regions may represent microcalcifications. Since common breast tissue patterns appear like ridges and lines, line patterns may be enhanced by using a gray-scale mathematical morphologic filter with linear structural elements [36]. Ridge patterns may be enhanced by using a shape index operator [37, 38]. The "impulsive" small high brightness regions may be extracted by using the following median-filter-based method. Since a median filter can remove impulsive noise, subtraction of a median-filtered image from the original image gives enhancement (or extraction) of impulsive noise (small regions or outliers). Half-thresholding may be performed on the subtracted median-filtered image so that only bright (greater than a predetermined threshold value) "impulsive" noise (small regions) retains. By changing the kernel size of the median filter, "impulsive" high-brightness regions of a certain size can be enhanced (extracted). For example, a median filter with a kernel of 25 pixels can remove "impulsive" small regions smaller than or equal to 12 pixels.

Applications of artificial neural network (ANN) techniques to medical pattern recognition and classification, called massive-training ANNs (MTANNs), are discussed in U.S. Pat. Nos. 6,819,790, 6,754,380, and 7,545,965, and U.S. Publication No. 2006/0018524. The MTANN techniques of U.S. Pat. Nos. 6,819,790 and 6,754,380, and U.S. Publication No. 2006/0018524 are developed, designed, and used for pattern recognition or classification, namely, to classify patterns into certain classes, e.g., classification of a region of interest in CT into an abnormal or normal. In other words, the final output of the MTANN is classes such as 0 or 1, whereas the final output of the methods and systems described in this patent specification, the PTNR, is continuous values (or images) or pixel values. The techniques of U.S. Pat. No. 7,545,965 are developed, designed, and used for enhancing or suppressing specific patterns such as ribs and clavicles in chest radiographs, whereas a PTNR is used for converting lower-dose mammograms to higher-dose-like mammograms.

In another implementation example of designing PTNR, simulated lower-dose mammograms may be used instead of using real lower-dose mammograms. This implementation starts with higher-dose mammograms with less noise. Simulated mammographic noise is added to the higher-dose mammograms. Noise in mammograms has two different types of noise components: quantum noise and electronic noise. Quantum noise in x-ray images can be modeled as signal-dependent noise, while electronic noise in x-ray images can be modeled as signal-independent noise. To obtain simulated lower-dose mammograms, simulated quantum and electronic noise is added to the higher-dose mammograms.

In further examples, PTNR may be combined with other image-processing or pattern-recognition techniques, for example, a classifier such as a multi-layer perceptron, a support vector machine, linear discriminant analysis, or quadratic discriminant analysis.

The input lower-dose mammograms and the desired higher-dose mammograms preferably correspond to each other, namely, the location and orientation of the breast tissue are the same or very close in both images. This can be accomplished easily when a breast phantom is used. In some examples, the correspondence may be essentially exact, e.g., the lower-dose and higher-dose mammograms taken at the same time or right after one another of the same patient or a breast phantom. In other examples, the lower-dose and higher-dose mammograms may be taken at different magnifications or different times. In such cases, an image registration technique may be needed and used to match the locations of objects in the two mammograms. The image registration may be rigid registration or non-rigid registration.

Mammograms discussed here may be mammograms taken on a full field digital mammography system. a digital mammography system, or a film-screen mammography system. They may be digitized screen film mammograms.

Experiments

Figure 6:
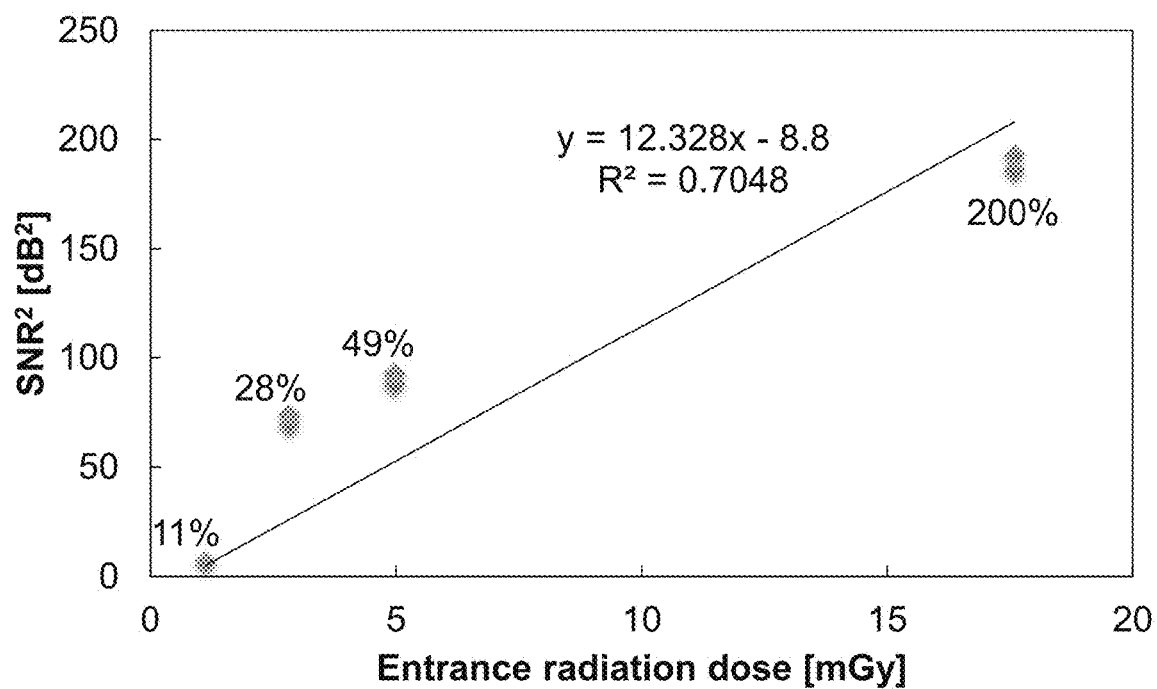
FIG. 6 shows the relationship between entrance radiation dose [mGy] and the image quality in the square of the SNR.

In order to design and evaluate an example of PTNR, six mammograms were acquired of an anthropomorphic (ham) breast phantom at six different radiation dose levels with a full field digital mammography system (Aspire H D, Fujifilm USA, Inc., Valhalla, N.Y.). The radiation doses were changed by changing tube current-time product, while the tube voltage was fixed at 27.9 kVp. The tube current-time products and the corresponding tube currents in the acquisitions were as follows: 5, 12.5, 22, 45, 90, and 140 mAs; 19, 24, 43, 81, 133 and 133 mA, respectively. Other acquisition conditions were as follows: a spatial resolution (pixel size) was 20 pixels/mm (0.05 mm/pixel): the matrix size of an image was 5,928×4,728 pixels; and the bit depth was 14 bits. Mammograms of the ham phantom at 11, 28, and 100% of the standard dose of 10 mGy are illustrated in FIG. 5(a) through 5(c). Signal-to-noise ratio (SNR) [dB] and improvement in SNR (ISNR) [dB] [39, 40] were used to measure the image quality. The relationship between entrance radiation dose [mGy] and the image quality in the square of the SNR is shown in FIG. 6. Regression analysis showed that radiation dose was directly proportional to the square of the SNR approximately ($R^2$=0.70).

Two PTNR schemes (PTNR 11 and PTNR28) were trained under two different low-dose conditions: The PTNR11 was trained with an input lower-dose (5 mAs, 28 kVp, 1.1 mGy in entrance dose, 11% of the standard dose) mammogram of a ham phantom and the corresponding higher-dose (140 mAs, 28 kVp, 300% of the standard dose) mammogram. The PTNR28 was trained with an input lower-dose (12.5 mAs, 28 kVp, 2.8 mGy in entrance dose, 28% of the standard dose) mammogram of the same ham phantom and the same corresponding higher-dose (300% of the standard dose) mammogram. The input images used for training of the PTNR11 and PTNR28 are shown in FIGS. 5 (a) and (b), respectively, while the desired image used for training of the PTNR11 and PTNR28 is shown in FIG. 5(d). The corresponding standard-dose mammogram of the ham phantom is shown as a reference in FIG. 5(c).

Figure 7A:
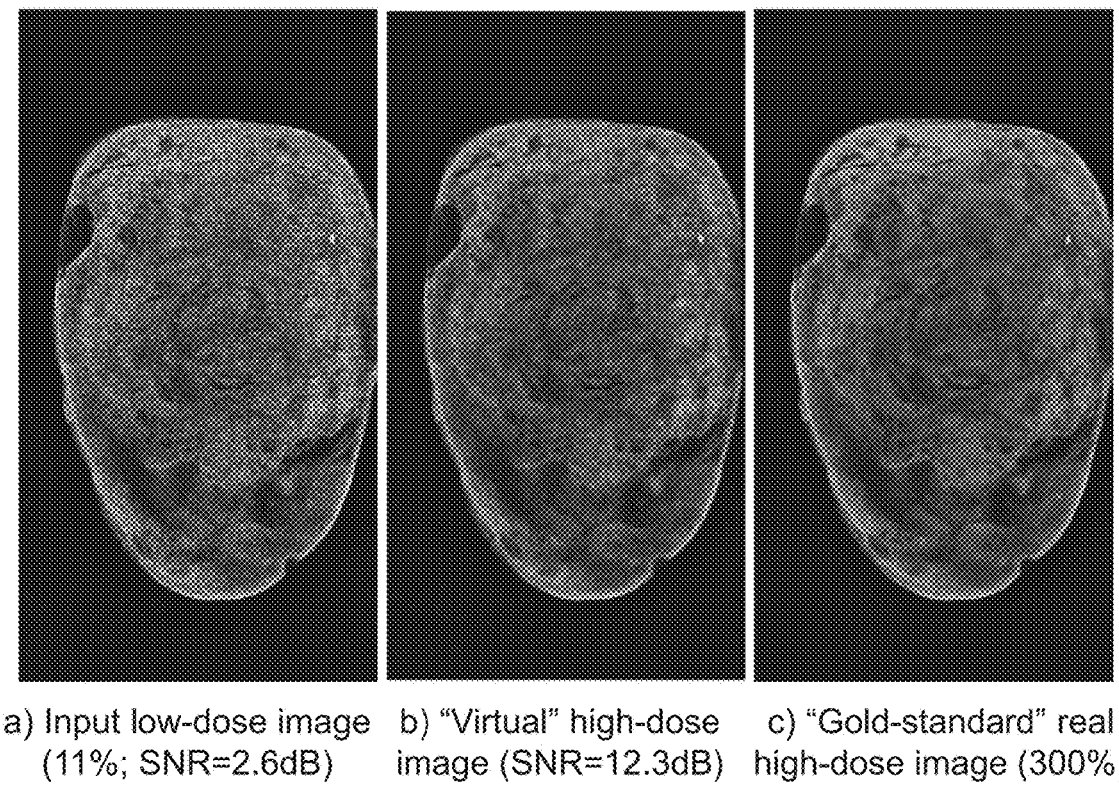
FIGS. 7A and 7B show input low-dose mammograms, "virtual" high-dose mammograms obtained by using the PTNR11 and PTNR28, respectively, and "gold-standard" high-dose mammograms for the ham phantom.
Figure 7B:
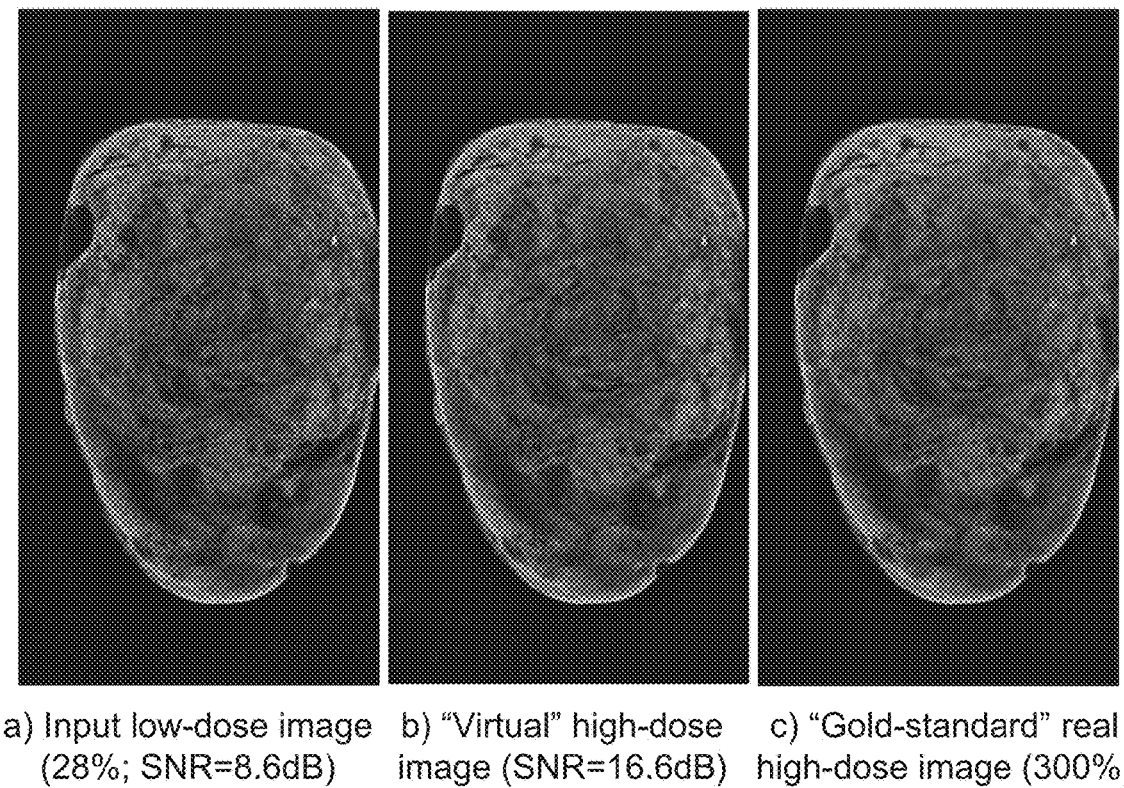

The trained PTNR11 and PTNR28 were applied to a non-training low-dose (5 mAs, 28 kVp, 1.1 mGy, 11% of the standard dose) mammogram and a non-training low-dose (12.5 mAs, 28 kVp, 2.8 mGy, 28% of the standard dose) mammogram. The trained PTNR11 and PTNR28 were able to convert the non-training low-dose mammograms with SNRs of 2.6 and 8.6 dB, respectively, to "virtual high-dose" mammograms with SNRs of 12.3 and 16.6 dB, respectively. The PTNR11 and PTNR28 achieved ISNRs of 9.7 and 8.0 dB, respectively. Noise in the input low-dose mammograms is reduced substantially in the "virtual" high-dose mammograms by the PTNRs, while details of structures are maintained, as shown in FIGS. 7A and 7B. Note that the SNR of "virtual high-dose" mammograms obtained by the present inventions may be about 30, 25, 20, 15, 14, 13, 12, 11, 10, 9, 8, 7, 6, 5, 4, 3, 2, or 1 dB higher than the original low-dose mammograms.

Figure 8:
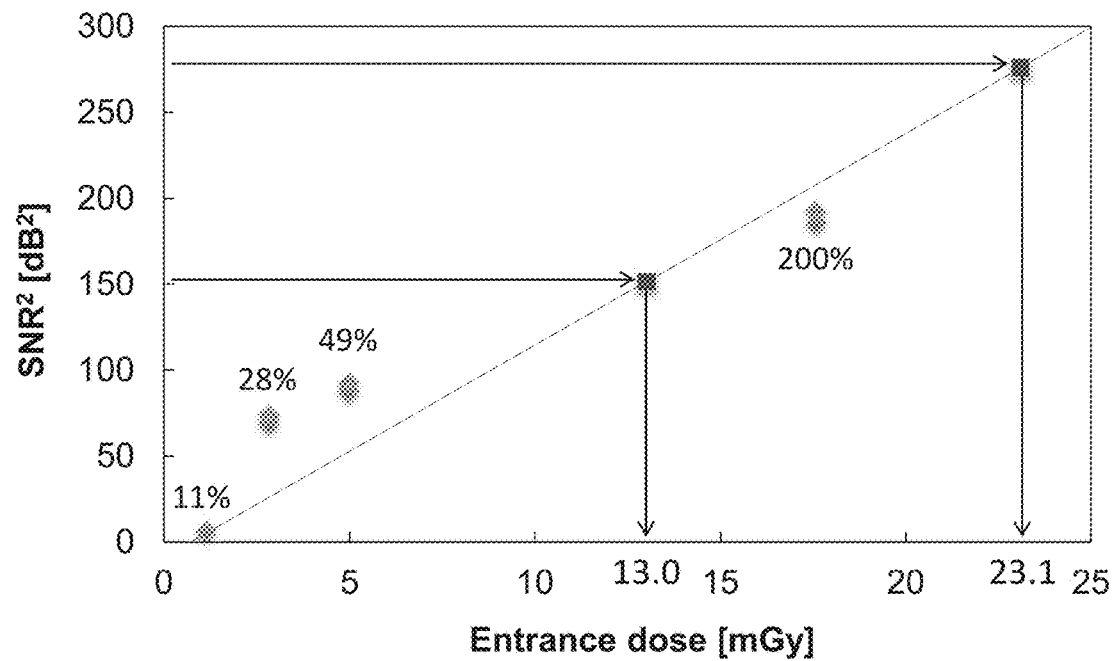
FIG. 8 shows estimates for entrance radiation dose equivalent to that of a real, high-dose mammogram by using a relationship between radiation dose and image quality.

Estimates were calculated for the entrance radiation dose equivalent to that of a real high-dose mammogram by using the relationship between radiation dose and image quality in FIG. 6. The results indicate that the "virtual" high-dose mammograms obtained by the PTNR11 and PTNR28 are equivalent to 13.0 and 23.1 mGy real high-dose mammograms, respectively, as shown in FIG. 8. Thus, the PTNR11 and PTNR28 reduced radiation dose from 13.0 and 23.1 mGy to 1.1 and 2.8 mGy, respectively, namely, reduction in radiation dose by 91 and 88%, respectively.

Thus, the study results with anthropomorphic (ham) breast phantoms demonstrated that the PTNR technology would be able to reduce radiation dose by 88-91%.

To evaluate the performance of PTNR technology, the PTNR trained with another anthropomorphic breast phantom (Gammex 169 "Rachel", Gammex R M I, Middleton, Wis.). Ten mammograms of the anthropomorphic breast phantom were acquired at ten different radiation dose levels for the input to the PTNR with a full field digital mammography system (Aspire H D, Fujifilm USA, Inc., Valhalla, N.Y.). The radiation doses were changed by changing tube current-time product, while the tube voltage was fixed at 27.9 kVp. The tube current-time products and corresponding entrance doses in the acquisitions were as follows: 12, 28, 56, 80, 109, 139, 159, 199, 218, and 278 mAs; 1.5, 3.4, 6.8, 9.7, 13.4, 17.1, 19.5, 24.4, 26.8, and 34.1 mGy, respectively. The tube currents in the acquisitions ranged from 24-133 mA.

Ten more mammograms of the anthropomorphic breast phantom were acquired at the highest radiation dose level ten times for the teaching desired higher-dose mammograms. The tube voltage, the tube current, the tube current-time product, and the entrance dose in the acquisitions were 30.9 kVp, 133 mA, 319 mAs, and 39.0 mGy, respectively. Other acquisition conditions were as follows: a spatial resolution (pixel size) was 20 pixels/mm (0.05 mm/pixel); the matrix size of an image was 4.740×3,540 pixels; and the bit depth was 14 bits.

Figure 9:
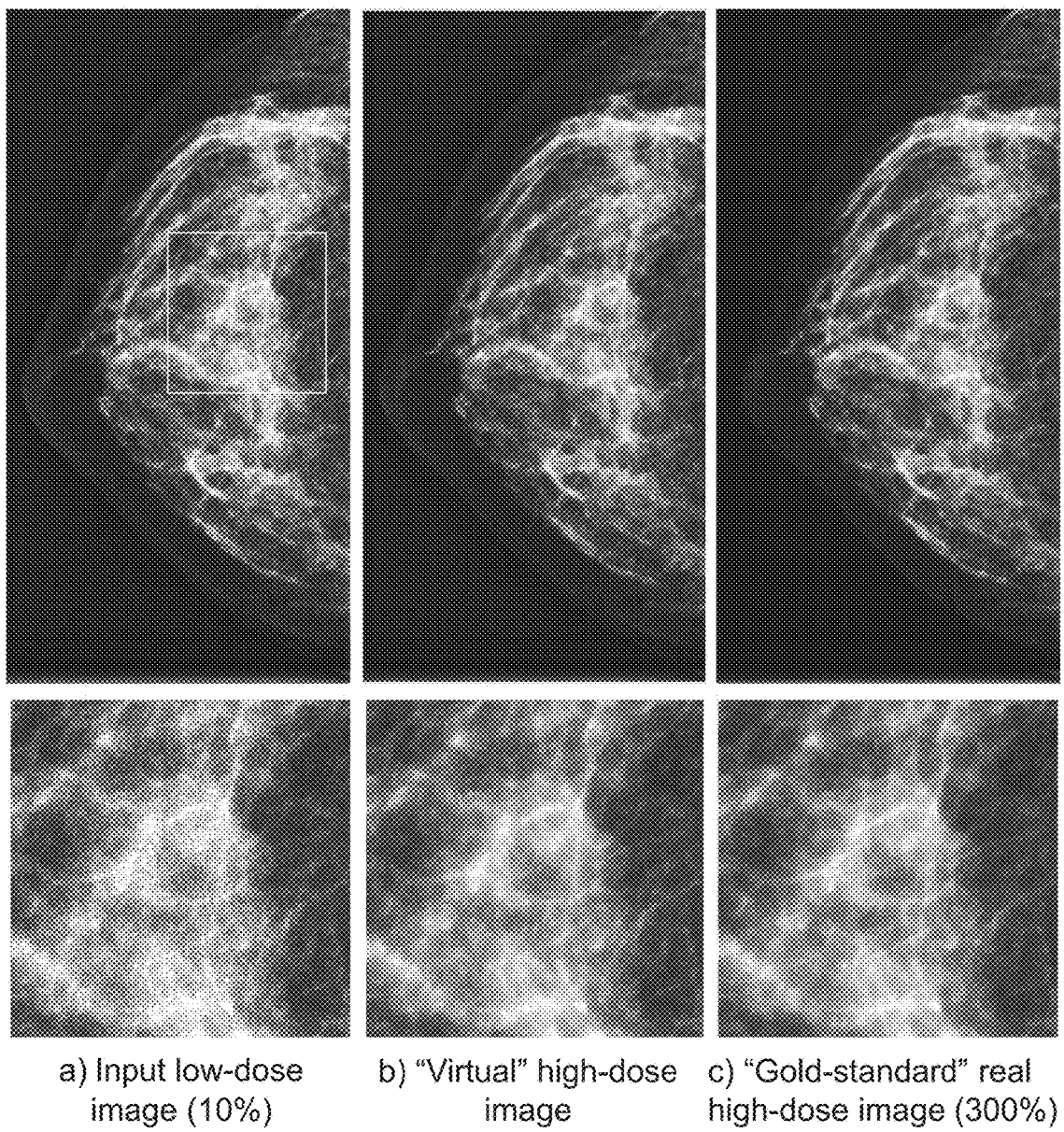
FIG. 9 shows the input low-dose mammogram, the "virtual" high-dose mammogram obtained by using the PTNR, and "gold-standard" high-dose mammogram for another anthropomorphic breast phantom.

Mammograms of the anthropomorphic breast phantom at 10 and 300% of the standard dose are illustrated in FIGS. 9(a) and (c). The PTNR was trained with the 10% dose mammogram as input and 300% dose mammogram as the desired teaching image. The output image, "virtual" high-dose image, from the trained PTNR is shown in FIG. 9(b). Noise in the input low-dose mammogram is reduced substantially in the "virtual" high-dose mammogram by the PTNR, which are similar to the "gold-standard" real high-dose mammogram, while details of breast tissue and structures are maintained.

To evaluate the performance and robustness of PTNR technology, the PTNR trained with the anthropomorphic breast phantom was applied to non-training 30 clinical cases. Each of the 30 patients had a low-dose (25% of the standard dose) mammogram in addition to the standard-dose (100%) mammogram with a full field digital mammography system (Aspire H D, Fujifilm USA, Inc., Valhalla, N.Y.). The IRB protocol for this study has been approved, and the written patient consent was obtained from all 30 patients. The low dose mammograms were obtained by changing tube current-time product, while the tube voltages were at approximately 30 kVp, more precisely ranging from 29-31 kVp. The tube current, tube current-time product, and entrance dose for standard-dose mammograms ranged from 118-122 mA, 98-132 mAs, and 3.6-6.2 mGy, respectively, whereas those for low-dose mammograms ranged from 40-56 mA, 20-28 mAs, and 1.0-1.6 mGy, respectively. Other acquisition conditions were as follows: a spatial resolution (pixel size) was 20 pixels/mm (0.05 mm/pixel); the matrix size of an image was 4.740×3,540 pixels; and the bit depth was 14 bits.

Figure 10:
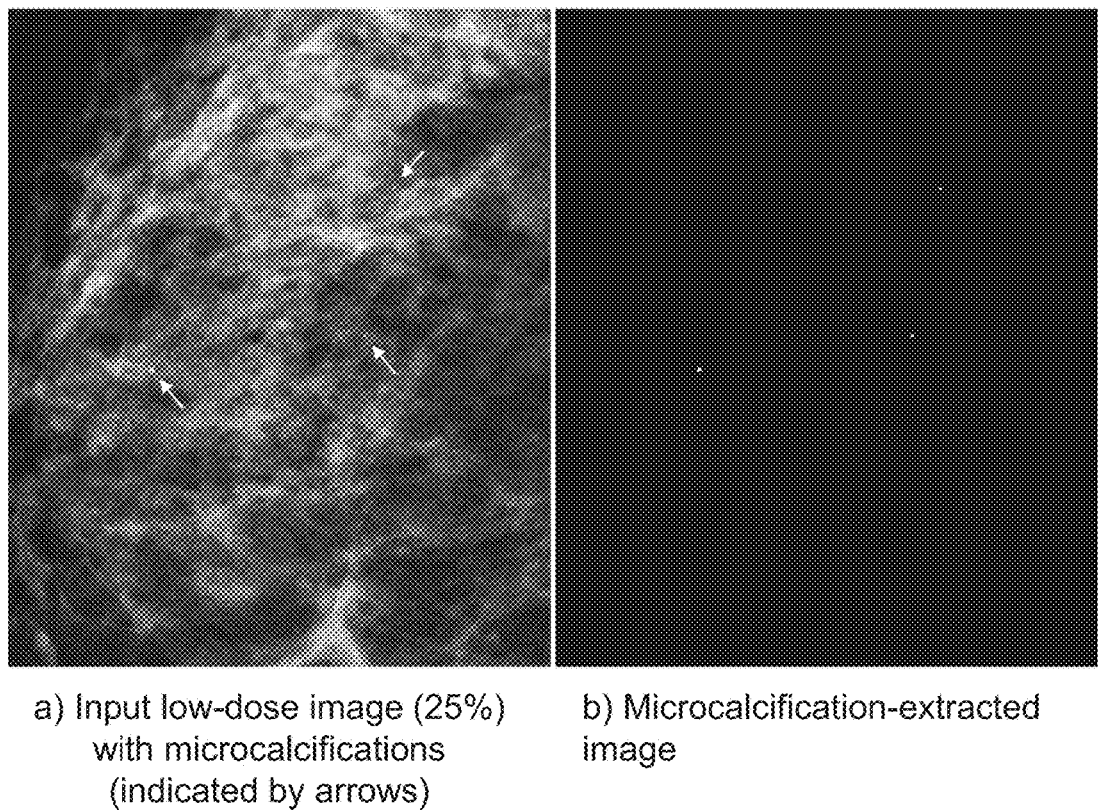
FIG. 10 illustrates the input low-dose (25% of the standard dose) mammogram with microcalcifications (indicated by arrows) for a clinical patient case and the microcalcification-extracted image obtained by using the extractor for "impulsive" small high brightness regions.
Figure 11:
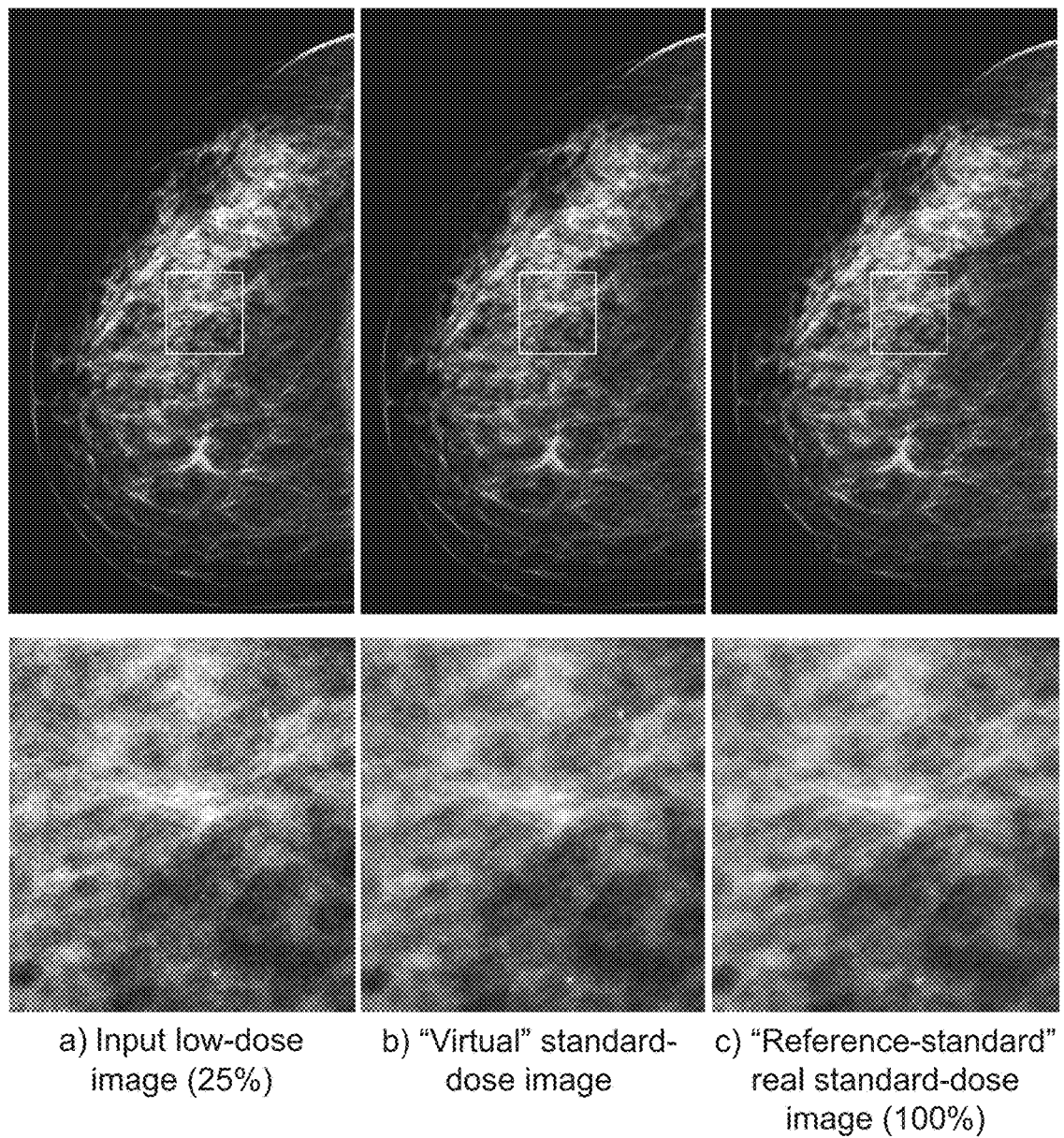
FIG. 11 shows the input low-dose (25% of the standard dose) mammogram, the "virtual" standard-dose mammogram obtained by using the PTNR, and "reference-standard" standard-dose mammogram for a clinical patient case.

The extractor for "impulsive" small high brightness regions was able to extract microcalcifications in the low-dose (25% of the standard dose) clinical mammograms, as illustrated in FIG. 10. The trained PTNR was able to convert the non-training low-dose (25% of the standard dose) clinical mammograms to "virtual standard-dose" mammograms with less noise, as illustrated in FIG. 11. Noise in the input low-dose mammograms is reduced substantially in the "virtual" standard-dose mammograms by the PTNR, while details of structures are maintained, as demonstrated in FIG. 11(b). The virtual standard-dose mammograms are similar to "reference-standard" real standard-dose mammograms, as demonstrated in FIGS. 11(b) and (c).

The processing time of the conversion process by the PTNR in the above example was 43 seconds for each image on a single-core ordinary PC (Intel Xeon at 2.2 GHz). Since the algorithm of the PTNR is parallelizable, it can be shortened to 3.6 sec. on a computer with 2 hexa-core processors, and shortened further with faster or specialized firmware/hardware.

The PTNR technology described in this patent specification may be implemented in a medical imaging system such as a digital mammography system, a full field digital mammography system, and a screen film mammography system. The PTNR may be implemented in a computer system or a viewing workstation. The PTNR may be coded in software or hardware. The PTNR may be coded with any computer language such as C, C++, Basic, C#, Matlab, python, Fortran, Assembler, Java, and IDL. The PTNR may be implemented in the Internet space, cloud-computing environment, or remote-computing environment. Converted images may be handled and stored in the Digital Imaging and Communications in Medicine (DICOM) format, and they may be stored in a picture archiving and communication system (PACS).

Figure 12:
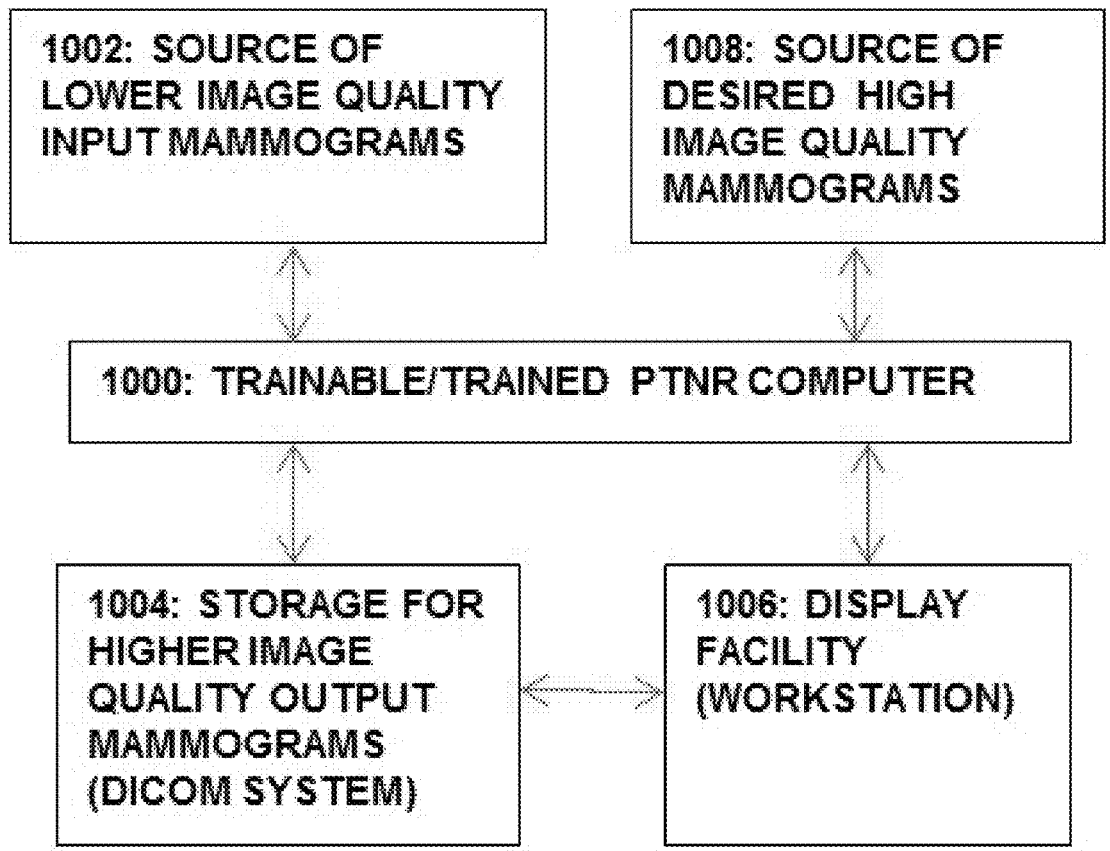
FIG. 12 illustrates in block diagram form a system for training a PTNR to convert lower image quality input mammograms into higher image quality output mammograms or, alternatively, a trained PTNR system for converting lower image quality input mammograms into higher image quality output mammograms and for storing or otherwise utilizing the output mammograms.

FIG. 12 illustrates in block diagram form a system training a PTNR computer or using a trained PTNR computer. When using a trained PTNR computer 1200, a source 1202 provides lower image quality input mammograms, such as mammograms taken at radiation dose that is lower than a standard radiation dose for conventional mammograms. Source 1202 can be a conventional mammography unit, such as a digital mammography system that is set to take breast images at lower dose, or any other source of digital or digitized mammograms that have been taken at lower-than-standard dose or otherwise have lower image quality that if they had been taken at a standard dose for conventional mammograms. For example, source 1202 is arranged to take low-dose mammograms at a dose that is between approximately 3.0 mGy and 0.3 mGy for 2-view imaging of each breast of a patient, between approximately 90% and 10% of the x-ray doses for standard mammograms, or between approximately 50% and 10% of the x-ray doses for standard mammograms. PTNR computer 1200 is programmed and configured to apply the processes described above to convert input mammograms into output mammograms that have higher image quality, and supplies the output mammograms to a storage system such as hospital DICOM PACS facility and/or to a display unit 1206 such as conventional workstation commonly used in hospitals to view medical images provided from the DICOM PACS facility or directly from a medical imaging device or from some other source. When the system of FIG. 12 is used to train PTNR computer 1200, source 1202 supplies lower image quality input mammograms that may have been taken at lower-than-standard radiation dose and/or may have resulted from deliberately degrading the image quality of standard-dose (or higher-dose) mammograms, and a source 1208 supplies matching desired mammograms. The desired mammograms may be actual mammograms taken at a radiation dose that is substantially higher than that used to take the input mammograms, for example at the dose recommended by MQSA for standard screening mammograms or a higher dose. Each input mammogram is paired with a respective desired mammogram. Using the processes described above, PTNR computer 1200 is trained to produce an output mammogram from an input mammogram, then compare the output mammogram with the respective desired mammogram, then adjust process parameters to reduce the difference between the output mammogram and the desired mammogram, and repeat these steps until the difference is less than a threshold or some other condition is met, such as exceeding a set number of iterations or reaching a selected threshold of the difference. The process parameters in the state at which iterations stop can become the parameters for a trained PTNR computer 1200, and used thereafter to convert actual lower image quality input mammograms into higher image quality output mammograms. From time to time in the operation of a trained PTNR computer 1200, a refreshing training process can be used. If a system is used solely with a trained PTNR computer 1200, the parameters for the converting process can be pre-stored in computer 1200, and can be updated or improved from time to time by replacement with a new set of parameters for the conversion processes.

The image conversion processes described above can be carried out through the use of a trainable/trained computer 1200 that is programmed with instruction downloaded from a computer program product that comprises computer-readable media such as one or more optical discs, magnetic discs, and flash drives storing, in non-transitory form, the necessary instructions to program computer 1200 to carry out the described processes involved in training the computer and/or using the trained computer to convert low image quality input mammograms into higher image quality mammograms. The instructions can be in a program written by a programmer of ordinary skill in programming based on the disclosure in this patent specification and the material incorporated by reference, and general knowledge in programming technology.

While several embodiments are described, it should be understood that the technology described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features or other described embodiments. Further, like reference numbers and designations in the various drawings indicate like elements. There can be alternative ways of implementing both the processes and systems described herein that do not depart from the principles that this patent specification teaches. Accordingly, the present embodiments are to be considered as illustrative and not restrictive, and the body of work described herein is not to be limited to the details given herein, which may be modified within the scope and equivalents of the appended claims.

What is claimed:

1. A method of processing a mammogram, comprising:
obtaining a lower image quality input mammogram from a system;
acquiring plural image patches from the input mammogram where each patch comprises a respective group of pixels;
entering the image patches into a computer-implemented, trainable regression model as input and obtaining from the model output pixel values corresponding to respective image patches using a process that derives an output pixel from each respective input patch;
wherein the trainable regression model has been trained through computer processing to convert known lower image quality mammograms to known higher image quality mammograms; and
arranging the output pixel values from the regression model into a desired output mammogram of higher image quality than the input mammogram;
wherein the output pixels of the desired output mammogram are spatially arranged in relation to the spatial arrangement of the image patches of the input mammogram.

2. The method of claim 1, wherein the input mammogram is relatively low dose mammogram.

3. The method of claim 1, wherein the input mammogram is obtained from one or more of a mammography system, computer storage, a viewing workstation, a picture archiving and communication system, cloud computing, website, and the Internet.

4. The method of claim 3, wherein the mammography system is operated in a low-dose mode.

5. The method of claim 1, wherein the trainable regression model is a previously-trained regression model that has been trained by extracting patches of pixels from a training input mammogram, deriving from each extracted patch a respective training output pixel value based on parameters of the regression model, comparing the training output pixel values with the values of respective pixels of a desired mammogram, and adjusting the parameters of the regression model to reduce differences between the training output pixels and the respective pixels of the desired mammogram until a threshold condition is met.

6. The method of claim 1, wherein the trainable regression model is at least one of an artificial neural network regression model, a support vector regression model, a nonlinear Gaussian process regression model, and a machine-learning regression model.

7. The method of claim 1, wherein the trainable regression model is a trainable regression model that was trained with lower image quality mammograms and higher image quality mammograms.

8. The method of claim 7, wherein the lower-quality mammograms are lower-dose mammograms, and the higher-quality mammograms are higher-dose mammogram.

9. The method of claim 1, wherein the input mammogram is taken at 45 mAs or below.

10. The method of claim 1, wherein the input mammogram is taken at 15 mAs or below.

11. The method of claim 1, further comprising:
extraction of morphologic elements that extracts morphologic elements from the input mammogram so that:

the plural image patches are acquired from the input mammogram and the morphologic-elements-extracted image.

12. The method of claim 11, wherein the extraction of morphologic elements includes extraction of small high brightness regions.

13. The method of claim 11, wherein the size of the plural image patches acquired from the input mammogram is larger than or equal to the size of the plural image patches acquired from the morphologic-elements-extracted image.

14. A method of processing a mammogram, comprising:
obtaining a pair of an input mammogram and a desired mammogram from a system;
acquiring plural image patches from the input mammogram where each patch comprises a group of pixels;
entering the image patches into a computer-implemented, trainable regression model as input;
converting each patch of pixels of the input mammogram into a respective training output pixel value based on parameters of the regression model;
calculating differences between the training output pixel values from the trainable regression model and corresponding desired pixel values from the desired mammogram; and
adjusting parameters in the trainable regression model based on the calculated differences to reduce the differences and repeating the converting and calculated steps using the adjusted parameters until a threshold condition is met.

15. The method of claim 14, wherein the input mammogram is relatively low dose mammogram and the desired mammogram is relatively high dose mammogram.

16. The method of claim 14, wherein the input mammogram is relatively low quality mammogram and the desired mammogram is relatively high quality mammogram.

17. The method of claim 14, wherein at least one of the mammograms is obtained from one of a mammography system, computer storage, a viewing workstation, a picture archiving and communication system, cloud computing, website, and the Internet.

18. The method of claim 17, wherein the mammography system is configured to operate in a lower dose mode and in a higher dose mode.

19. The method of claim 14, wherein the trainable regression model is one of an artificial neural network regression model, a support vector regression model, nonlinear Gaussian process regression model, and a machine-learning regression model.

20. The method of claim 14, wherein the input mammogram is taken at a radiation dose that is at least 50% lower than the dose for the desired mammogram.

21. The method of claim 14, wherein the input mammogram is taken at a radiation dose that is at least 75% lower than the dose for the desired mammogram.

22. The method of claim 14, wherein the input mammogram is taken at a radiation dose that is at least 90% lower than the dose for the desired mammogram.

23. The method of claim 14, wherein the image patch includes at least 2 by 2 pixels.

24. The method of claim 14, wherein the differences comprise a mean absolute error between training output pixel values and corresponding desired pixel values, or a mean squared error between training output pixel values and corresponding desired pixel values.

25. The method of claim 14, wherein the adjusting parameters in the trainable regression model comprise at least one of an error-back propagation algorithm, a steepest descent method, Newton's algorithm, and an optimization algorithm.

26. The method of claim 14, further comprising:
extraction of morphologic elements that extracts morphologic elements from the input mammogram; and
wherein the plural image patches are acquired from the input mammogram and the morphologic-elements-extracted image.

27. The method of claim 26, wherein the extraction of morphologic elements includes extraction of small high brightness regions.

28. The method of claim 26, wherein the size of the plural image patches acquired from the input mammogram is larger than or equal to the size of the plural image patches acquired from the morphologic-elements-extracted image.

29. A system comprising:
a source of a lower image quality input mammogram;
a computer-implemented processor configured to acquire plural image patches from the input mammogram where each patch comprises a group of pixels;
said processor being further configured to apply a trained regression model processing to the acquired image patches and provide output pixel values each corresponding to a respective image patch;
wherein the trainable regression model has been trained through computer processing to convert lower quality mammograms into higher quality mammograms;
said processor being further configured to arrange the output pixel values from the regression model into an output mammogram that has a higher image quality than the input mammogram;
wherein the output pixels are arranged in the output at locations corresponding to the locations in the input mammogram of the patches that provided the pixel values of the respective output pixels; and
a display associated with the processor to receive and display the output mammogram.

30. A system comprising:
a source configured to provide a pair of an input mammogram and a desired mammogram;
a computer-implemented trainable regression model facility configured to acquire plural image patches from the input mammogram, each patch comprising a group of pixels, and apply regression model processing thereto to produce an output mammogram comprising pixel values each derived from a respective image patch of the input mammogram, calculate a difference between the input mammogram and the output mammogram and change parameters of the regression model to reduce the difference, and repeat the steps of applying the regression model, calculating the difference and changing parameters until a threshold condition is met, and outputting a final output mammogram upon meeting the threshold condition; and
a display facility selectively displaying the final output mammogram.

31. A computer program product comprising instructions stored in a non-transitory computer-readable media that, when loaded into and executed by a computer system cause the computer system to carry out the process of:
obtaining a lower image quality input mammogram;
acquiring plural image patches from the input mammogram where each patch comprises a group of pixels;

entering the image patches into a trainable regression model as input and obtaining from the model output pixel values each corresponding to a respective image patch;

wherein the trainable regression model has been trained by extracting patches of pixels from a training input mammogram, deriving from each extracted patch a respective training output pixel value based on parameters of the regression model, comparing the training output pixel values with the values of respective pixels of a desired mammogram, and adjusting the parameters of the regression model to reduce differences between the training output pixels and the respective pixels of the desired mammogram until a threshold condition is met; and arranging the output pixel values from the regression model into an output mammogram of higher image quality than the input mammogram.

32. The system of claim 29 in which the source of lower image quality mammograms comprises a low x-ray dose breast imaging structure configured to image patients' breasts with an x-ray beam to provide said low-dose x-ray breast images, each of which is of the taken at an x-ray dose substantially below that for a standard mammogram and having image quality significantly below that of a standard mammogram.

33. The system of claim 32 in which the breast imaging structure is configured to take the low-dose x-ray images at doses corresponding to the dose of approximately 3.0 mGy and 0.3 mGy for 2-view imaging of each breast of a patient.

34. The system of claim 32 in which the x-ray breast imaging system is configured to take the low-dose x-ray images at doses that are between approximately 90% and 10% of the x-ray doses for standard mammograms.

35. The system of claim 32 in which the breast imaging structure is configured to take the low-dose x-ray images at dose that are between approximately 50% and 10% of the x-ray doses for standard mammograms.

36. The system of claim 32 in which the processor is configured to process the low-dose images by processing each of respective multi-pixel patches of the low-cost images into a single pixel of the higher-quality images.

37. The system of claim 32 in which the processor is further configured to extract morphologic elements corresponding to impulse areas of the low-dose images and use the extracted elements to improve converting the low-dose images into the higher-quality images.

* * * * *